United States Patent
West et al.

(10) Patent No.: US 6,530,944 B2
(45) Date of Patent: Mar. 11, 2003

(54) OPTICALLY-ACTIVE NANOPARTICLES FOR USE IN THERAPEUTIC AND DIAGNOSTIC METHODS

(75) Inventors: Jennifer L. West, Pearland, TX (US); Nancy J. Halas, Houston, TX (US); Leon R. Hirsch, Houston, TX (US)

(73) Assignee: Rice University, Houston, TX (US)

(*) Notice: Subject to any disclaimer, the term of this patent is extended or adjusted under 35 U.S.C. 154(b) by 0 days.

(21) Appl. No.: 09/779,677

(22) Filed: Feb. 8, 2001

(65) Prior Publication Data

US 2002/0103517 A1 Aug. 1, 2002

Related U.S. Application Data

(60) Provisional application No. 60/181,109, filed on Feb. 8, 2000, and provisional application No. 60/222,437, filed on Aug. 1, 2000.

(51) Int. Cl.[7] .................................................. A61N 5/06
(52) U.S. Cl. ........................... 607/88; 607/100; 424/497
(58) Field of Search ........................ 607/88, 89, 92, 607/94, 103; 604/20; 606/2, 10, 14, 15, 33; 424/497, 490; 428/403

(56) References Cited

U.S. PATENT DOCUMENTS

| | | | |
|---|---|---|---|
| 5,213,788 A | | 5/1993 | Ranney |
| 5,411,730 A | * | 5/1995 | Kirpotin et al. ............ 424/322 |
| 5,427,767 A | | 6/1995 | Kresse et al. |
| 5,521,289 A | | 5/1996 | Hainfeld et al. |
| 5,990,479 A | | 11/1999 | Weiss et al. |
| 5,993,374 A | | 11/1999 | Kick |
| 6,048,515 A | | 4/2000 | Kresse et al. |
| 6,068,857 A | | 5/2000 | Weitschies et al. |
| 6,165,440 A | | 12/2000 | Esenaliev |
| 6,167,313 A | * | 12/2000 | Gray et al. .................. 607/103 |
| 6,180,415 B1 | | 1/2001 | Schultz et al. |
| 6,207,392 B1 | * | 3/2001 | Weiss et al. .................. 435/7.1 |
| 6,344,272 B1 | * | 2/2002 | Oldenburg et al. .......... 428/403 |
| 6,375,634 B1 | * | 4/2002 | Carroll ......................... 604/19 |
| 6,423,056 B1 | | 7/2002 | Ishikawa et al. |
| 6,428,811 B1 | | 8/2002 | West et al. |

OTHER PUBLICATIONS

R.P. Smith, *Photodynamic Therapy*, Curr Probl Cancer, Mar./Apr. 2002, 26:67–108.

C. Hopper, *Photodynamic therapy: a clinical reality in the treatment of cancer*, Lancet Oncol; Dec. 2000, 2:212–219.

P. Shum, et al., *Phototriggering of liposomal drug delivery systems*, Advanced Drug Delivery Reviews [Elsevier Science B.V.] 2001 53:273–284.

K. Maruyama, *In Vivo Targeting by Liposomes*, Biol. Pharm. Bull., Jul. 2000, 23(7) 791–799.

G. Bendas, *Immonuoliposomes—A Promising Approach to Targeting Cancer Therapy*, BioDrugs, 2001, 15(4):215–224.

S.R. Sershen, et al., *Temperature–sensitive polymer–nanoshell composites for photothermally modulated drug delivery*, World Biomaterials Congress 2000, Kamuela, HI, John Wiley & Sons, Inc., May/2000, 293–298.

J.L. West, et al., *Applications of nanotechnology to biotechnology*, Current Opinion in Biotechnology, 2000, 11:215–217.

(List continued on next page.)

*Primary Examiner*—Roy Gibson
(74) *Attorney, Agent, or Firm*—Fulbright & Jaworski L.L.P.

(57) ABSTRACT

This invention is generally in the field of improved methods for the localized delivery of heat and the localized imaging of biological materials. The delivery may be in vitro or in vivo and is useful for the localized treatment of cancer, inflammation or other disorders involving overproliferation of tissue. The method is also useful for diagnostic imaging. The method involves localized induction of hyperthermia in a cell or tissue by delivering nanoparticles to said cell or tissue and exposing the nanoparticles to an excitation source under conditions wherein they emit heat.

68 Claims, 9 Drawing Sheets

OTHER PUBLICATIONS

N.R. Jana, et al., *Seed–mediated growth method to prepare cubic copper nanoparticles*, Cur. Sci., Nov. 10, 2000, 79:9, 1367–1370.

S.S. Wong, *Narrow Mie Optical Cavity Resonances from Individual 100 nm Hematite Crystallites*, J. Phys. Chem., Dec 23, 2000, 105:3, 599–603.

M.C. Blanco, et al., *uv–vis Spectra Of Small Iron Particles*, IEEE Trans. Magnet., Mar 1994, 30:2, 739–741.

A. Bautista–Hernandez, et al., *Effect of thermal treatment on the optical properties of colloidal Cu nanoparticles prepared by ion–implantation in quartz glass*, Superficies y Vacio, Dec 1999, 9:296–299.

R.H. Magruder, III, et al., *Physical and optical properties of CU nanoclusters fabricated by ion implantation in fused silica*, J. Appl. Phys., Jul. 1994, 76:2, 708–715.

R.D. Averitt, *Plasmon Resonance Shifts of Au–Coated $Au_2S$ Nanoshells: Insight into Multicomponent Nanoparticle Growth*, Am. Phys. Soc., Jun. 2, 1997, 78:22, 4217–4220.

S.J. Oldenburg, et al., *Surface enhanced Raman scattering in the near infrared using metal nanoshell substrates*, J. Chem. Phys., Sep. 8, 1999, 111:10, 4729–4735.

S.J. Oldenburg, et al., *Infrared extinction properties of gold nanoshells*, Appl. Phys. Lett., Nov. 8, 1999, 75:19, 2897–2899.

R.D. Averitt, et al., *Optical Properties and Growth Kinetics of Au Coated $Au\_2S$ Nanoshells*, Session F7–Chemical Physics of Nanoparticles and Nanstructures II, Mar. 18, 2000, Web Publication.

S.J. Oldenburg, et al., *Self–assembled Metal Shell Nanoparticles*, Session E7–Chemical Physics of Nanoparticles and Nanostructures I, Mar. 18, 2000, Web Publication.

R.D. Averitt, et al., *Ultrafast electron dynamics in gold nanoshells*, Phys. Rev. B, Oct. 15, 1998, 58:16, R10 203–R10 106.

S.J. Oldenburg, et al., *Nanoengineering of Optical Resonances*, Chemical Physics Letters, 1998, 288, 243–347.

S.L. Westcott, *Formation and Adsorption of Clusters of Gold Nanoparticles onto Functionalized Silica Nanoparticle Surfaces*, Langmuir, 1998, 14:19, 5396–5401.

Averitt, et al. *Phys. Rev. Lett.*, 78:4217–20 (1997).

Oldenburg, et al., *Chem Phys. Lett.*, 288:243–47 (1998).

Averitt, et al., *J. Opt. Soc. Am. B.*, 6:787–792. (1999).

Gregorakis, et al., *Semin. Urol. Oncol.* 16(1):2–12 (1998).

Ozzello, et al., *Breast Cancer Res. Treat.* 48(2): 1354–7 (1998).

Bange, et al., *Nature Medicine.* 7(5):548–552 (2001).

Vriesendrop and Quadri. *Cancer Biotherapy & Radiopharmaceuticlas.* 15(5):431–445 (2000).

Chance, *Proc. Natl. Acad. Sci. U.S.A.* 90(8):3423–7 (1993).

Chen, et al. *Cancer letters.* 88:15–19 (1995).

Chen, et al. *Cancer letters.* 94:125–131 (1995).

Chen, et al. *Cancer letters.* 98: 169–173 (1996).

Chen, et al., *Cancer letters.* 115: 25–30 (1997).

B. Jeong, et al. *J. of Controlled Release* 62 (1999) 109–114.

Vrouenraets, et al. *Cancer Research* 59, 1505–1513, Apr. 1, 1999.

\* cited by examiner

OPTICALLY-ACTIVE NANOPARTICLES FOR USE IN THERAPEUTIC AND DIAGNOSTIC METHODS

This application claims priority to the U.S. Provisional Application, Serial No. 60/181,109, filed Feb. 8, 2000.

U.S. application Ser. No. 09/038,377, filed Apr. 10, 1998, U.S. application Ser. No. 60/222,437, filed Aug. 1, 2000; and PCT/US00/19268, filed Jul. 14, 2000 are specifically and fully incorporated by reference herein.

The invention was made with government support. The U.S. government may have certain rights in the invention.

BACKGROUND OF THE INVENTION

In many applications, it is desirable to target cells and tissue for localized heating or imaging. The therapeutic effects range from the destruction of cancerous cells and tumors, to the therapeutic or cosmetic removal of benign tumors and other tissue. Techniques which effect precise localized heating and illumination would allow one to enjoy therapeutic and diagnostic benefits, while minimizing the collateral damage to nearby cells and tissue. It is desirable that such techniques be amenable to both in vitro and in vivo therapeutic and diagnostic applications of induced hyperthermia and imaging, respectively, of cells and tissue.

A potentially useful in vivo application of such a technique would be in cancer reatment. For example, metastatic prostate cancer is a leading cause of mortality in American men. Estimates indicate that greater than one in every eleven men in the U.S. will develop prostate cancer. Accurate determination of the extent of local disease is often difficult. Methods for accurately detecting and imaging localized prostate disease are greatly needed. In addition, localized prostate cancer is generally treated with either radical prostatectomy or radiation therapy. Both of these procedures are plagued by significant morbidity. Minimally invasive treatment strategies with low associated morbidity should be feasible and would dramatically improve prostate cancer therapy.

A number of techniques have been investigated to direct therapeutic and diagnostic agents to tumors. These have included targeting of tumor cell surface molecules, targeting regions of activated endothelium, utilizing the dense and leaky vasculature associated with tumors, and taking advantage of the enhanced metabolic and proteolytic activities associated with tumors. Antibody labeling has been used extensively to achieve cell-selective targeting of therapeutic and diagnostic agents. A number of approaches have been taken for antibody-targeting of therapeutic agents. These have included direct conjugation of antibodies to drugs such as interferon-alpha (Ozzello, et al., 1998), tumor necrosis factor (Moro, et al., 1997), and saporin (Sforzini, et al., 1998). Antibody conjugation has also been used for tumor-targeting of radioisotopes for radioimmunotherapy and radioimmunodetection (Zhu, et al., 1998). Currently, there is a commercial product for detection of prostate cancer (ProstaScint) that is an antibody against prostate-specific membrane antigen conjugated to a scintigraphic target (Gregorakis, et al., 1998). Immunoliposomes or affinity liposomes are liposome drug carriers with antibodies conjugated to their surfaces. These drug carriers can be loaded with cytotoxic agents, such as doxorubicin, for destruction of cancerous cells. Antibody targeting is also under investigation for cell-selective gene therapy.

Virus particles have been developed that display single chain antibodies on their surface, allowing specific targeting of a wide variety of cell types (Yang, et al., 1998; Jiang, et al., 1998; Chu & Dornburg, 1997; Somia, et al., 1995). To target regions of activated endothelium, immunoliposomes have been made with antibodies to E-selectin on their surfaces. It may be possible to achieve similar targeting efficiencies with small tumor-specific peptides (Pasqualini, et al., 1997). Recently, tumors have been imaged using protease-activated near-infrared fluorescent probes (Weissleder, (1999). These agents could be administered systemically, were accumulated in the tumors due to the abundant and leaky vasculature, and were activated by the elevated proteolytic enzymes.

The nanoparticles that are the subject of this invention are amenable to these types of targeting methodologies. The nanoparticle surfaces can easily be modified with antibodies, peptides, or other cell-specific moieties. A specific embodiment of these nanoparticles act as absorbers of radiation. These nanoparticles have tunable excitation wavelengths and undergo nonradiative decay back to the ground state by emission of heat. This heat can be used to effect local hyperthermia. Alternatively, these nanoparticles, in addition to acting as absorbers, may scatter light and thereby act as contrast agents as a means to image the local environment in which they reside. Other nanoparticles that are also the subject of this invention are strong visible and infrared fluorophores. Their strong emission is used in imaging applications. It is known that solid metal nanoparticles (i.e. solid, single metal spheres of uniform composition and nanometer dimensions) possess interesting optical properties. In particular, metal nanoparticles display a pronounced optical resonance. Metal nanoparticles are similar to metal colloids in this regard, exhibiting a strong optical absorption due to the collective electronic response of the metal to light. Metal colloids have a variety of useful optical properties including a strong optical absorption and an extremely large and fast third-order nonlinear optical (NLO) polarizability. These optical properties are attributed to the phasic response of electrons in the metallic particles to electromagnetic fields. This collective electron excitation is known as plasmon resonance. At resonance, dilute metal colloid solutions have the largest electronic NLO susceptibility of known substances. However, the utility of these solutions is limited because their plasmon resonance is confined to relatively narrow wavelength ranges and cannot readily be shifted. For example, silver particles 10 nm in diameter absorb light maximally at approximately 355 nm, while similar sized gold particles absorb maximally at about 520 nm. These absorbance maximums are insensitive to changes in particle size and various dielectric coatings on the particles. However, the nanoparticles of this invention are more amenable to a directed shift in their plasmon resonance and hence absorption or scattering wavelengths tan these solid metal nanoparticles.

There have been earlier efforts for therapeutic uses of compositions that emit heat upon excitation, however, these are distinguishable from the present invention. In U.S. Pat. No. 4,983,159, Rand describes the induction of hyperthermia to a neoplasm using particles which exhibit a heating hysteresis when subjected to an alternating magnetic field. However, the particles used in the '159 patent are more properly described as microparticles and are much larger than the analogous nanoparticles used herein. U.S. Pat. Nos. 4,106,488 and 4,303,636 to Gordon describe particles of nanometer scale dimensions. However, the excitation source is different from that which is used herein and outside the scope of the present invention. As such, it is believed that the underlying physical excitation mechanisms of these earlier works differs from that of the present invention.

A serious practical limitation to realizing many applications of solid metal nanoparticles is the inability to position the plasmon resonance at technologically important wavelengths. For example, solid gold nanoparticles of 10 nm in diameter have a plasmon resonance centered at 520 nm. This plasmon resonance cannot be controllably shifted by more than approximately 30 nanometers by varying the particle diameter or the specific embedding medium.

One method of overcoming this problem is to coat small nonconducting particles with these metals. For example, the reduction of Au on $Au_2S$ (reduction of chloroauric acid with sodium sulfide) particles has been shown to red shift the gold colloid absorption maximum from 520 nm to between approximately 600 nm and 900 nm, depending on the amount of gold deposited on the $Au_2S$ core and the size of the core. Zhou, et al. (1994). The ratio of the core radius to shell thickness can be controlled by changing the reactant concentrations or by stopping the reaction. In this case, the diameter of the particle core is directly proportional to the red shift in the wavelength of light that induces gold plasmon resonance. However, gold-sulfide particle diameters are limited to sizes of approximately 40–45 nm with a thin gold shell (less than 5 nm). The limited size of the gold-sulfide particles of Zhou et al. limits the absorbance maximum to wavelengths no larger than 900 nm. (Averitt et al. 1997).

An additional limitation of such particles as defined by Zhou et al. is that both the core and the shell are grown as a result of a single chemical reaction, thus limiting the choice of the core material and the shell material to $Au_2S$ and Au respectively. In addition, only the ratio of the core radius to shell thickness may be controlled; independent control of the core radius and the shell thickness is not possible.

Nedeljkovic and Patel (1991) disclosed silver-coated silver bromide particles that are produced by intense UV irradiation of a mixture of silver bromide, silver, sodium dodecylsulfate (SDS) and ethylenediaminetetraacetic acid (EDTA). The Neideljkovic particles range in size from approximately 10 to 40 nm and are irregularly shaped, as determined by transmission electron microscopy. Predictably, the spectra obtained from these particle preparations are extremely broad.

U.S. Pat. No. 5,023,139, Birnboim et al. disclosed theoretical calculations indicating that metal-coated, semiconducting, nanometer-sized particles containing should exhibit third-order nonlinear optical susceptibility relative to uncoated dielectric nanoparticles (due to local field enhancement). Their static calculations were based on hypothetical compositions. In those embodiments theoretically proposed by Birnboim et al. that do in fact propose a metal outer shell, there is an additional requirement as to the specific medium in which they must be used in order to properly function.

However, Birnboim does not disclose methods for preparing the disclosed hypothetical compositions. Furthermore, Birnboim's calculations do not take into account surface electron scattering. Surface electron scattering strongly modifies the optical response of all metallic structures that possess at least one dimension smaller than the bulk electron mean free path (e.g. in Au at room temperature the bulk electron mean free path is about 40 nm). This effect reduces the local field enhancement factor that in turn reduces the resonant third order nonlinear optical susceptibility associated with the nanoshell geometry. See, Averitt et al., 1997. Since typical shell thicknesses for these compositions fall below 40 nm, Birnboim et al's theoretical calculations fail to account for this effect which is an important aspect of the optical response for functional metal nanoshells.

It is also possible to conduct targeted imaging using fluorescent probes that emit infrared light from an object of interest (e.g., tumor) in vivo (Weissleder, 1999; Pathankar et al., 1997). For imaging, we need to focus on fluorophores and scatterers. Scatterers can be used to drastically change the scattering coefficient (thus acting as an optical contrast agent) in a targeted tissue to allow imaging. Absorbers might potentially be used in this application as well.

It has been discovered that nanoparticles comprising one non-conducting or semiconducting core layer and at least one conducting shell layer, in which the shell layer is independently layered upon said core layer and the thickness of said shell layer is independent of the radius of said core layer, can be manufactured to have the characteristic that the thickness of said shell layer is less than that of a shell layer for which the nanoparticle has a plasmon resonance peak width described by a bulk dielectric function of the material comprising the shell layer. Similarly, these nanoparticles can be manufactured to have plasmon resonance peak widths that are independent of the thickness of the shell layer Methods and materials have previously been disclosed that can be used to shift the wavelength of maximum resonance of metal nanoparticles called nanoshells. These methods produce materials having defined wavelength absorbance maxima across the visible and infrared range of the electromagnetic spectrum. Particularly, such metal nanoshell composites have been constructed in a manner to allow a choice of core material, core dimensions, and core geometry independent of those criteria for the shell material. Compositions produced by these methods have relatively homogeneous structures and do not have to rely on suspension in a particular medium in order to exhibit their desired absorption characteristics. Of interest herein, these nanoshells overcome the optical limitations of the prior art and which have limited the therapeutic and diagnostic applications discussed above. Such materials were described in U.S. application Ser. No. 09/038,277, filed Apr. 10, 1998; which is specifically and fully incorporated by reference herein.

SUMMARY OF THE INVENTION

It is an object of the present invention to provide materials and methods for use in cell and tissue therapy. The primary object is a method for inducing a localized, targeted hyperthermia in such cell and tissue therapy. It is another object of the present invention to provide materials and methods for use in diagnostic imaging.

It is a further object of the present invention to provide methods for using these materials which are minimally invasive and efficacious without systemic side effects.

In the therapeutic embodiment, methods are described in which particles are administered to cells and/or tissue, which upon their exposure to light, effect the in vitro or in vivo, local heating of their immediate environment. In the preferred embodiment, the particles consist of a dielectric or semiconductor core and a conducting shell, the dimension of the particles is on a scale of tens to hundreds of nanometers, and the radiation used is infrared radiation.

In a preferred embodiment, the method is used to treat cancer. In an alternative embodiment, the method is applied to treat non-malignant tumors. In either of these embodiments, the method may be the sole method, or it may be used in combination with another therapy. In another embodiment, the method may be used for cosmetic enhancement.

In a preferred embodiment, the nanoparticle consists of a silica core and a gold shell. In an alternative embodiment, the nanoparticle consist of a gold sulfide core and a gold shell.

In a further embodiment of the general method, the nanoparticles are targeted to a desired location through the use of appropriate chemical schemes. In the preferred embodiment, antigen-antibody binding is used for targeting.

In the diagnostic embodiment, methods are described in which particles are administered to cells and/or tissue, which upon their exposure to radiation, effect the in vitro or in vivo, imaging of their immediate environment. In the preferred embodiment, the particles consist of a dielectric or semiconductive core doped with rare earth ions such as $Pr^{+3}$, $Er^{+3}$, and $Nd^{+3}$, the dimension of the particles is on a scale of tens to hundreds of nanometers, and the radiation used is visible or infrared radiation. Alternatively, the particle may consist of dielectric or semiconductor core and a conducting shell.

In a preferred embodiment, the nanoparticle consists of a silica nanoparticle doped with $Pr^{+3}$ ions. In an alternative embodiment, the nanoparticle consists of a silica nanoparticle doped with $Er^{+3}$ or $Nd^{+3}$. In an alternative embodiment, the nanoparticle consists of a silica core with a gold shell designed as either an absorber or a scatterer.

In both the diagnostic and therapeutic embodiments, the radiation source is preferably electromagnetic radiation, but may alternatively be a non-electromagnetic radiation, such as ultrasound radiation.

BRIEF DESCRIPTION OF THE DRAWINGS

FIG. 8a is the control and 8b is the sample treated with nanoshells. The experimental procedure and results are described in Example 8.

FIG. 9a illustrates the histological section at magnification 200×. FIG. 9b illustrates the histological section at magnification 400×.

DETAILED DESCRIPTION OF THE INVENTION

Figure 1:
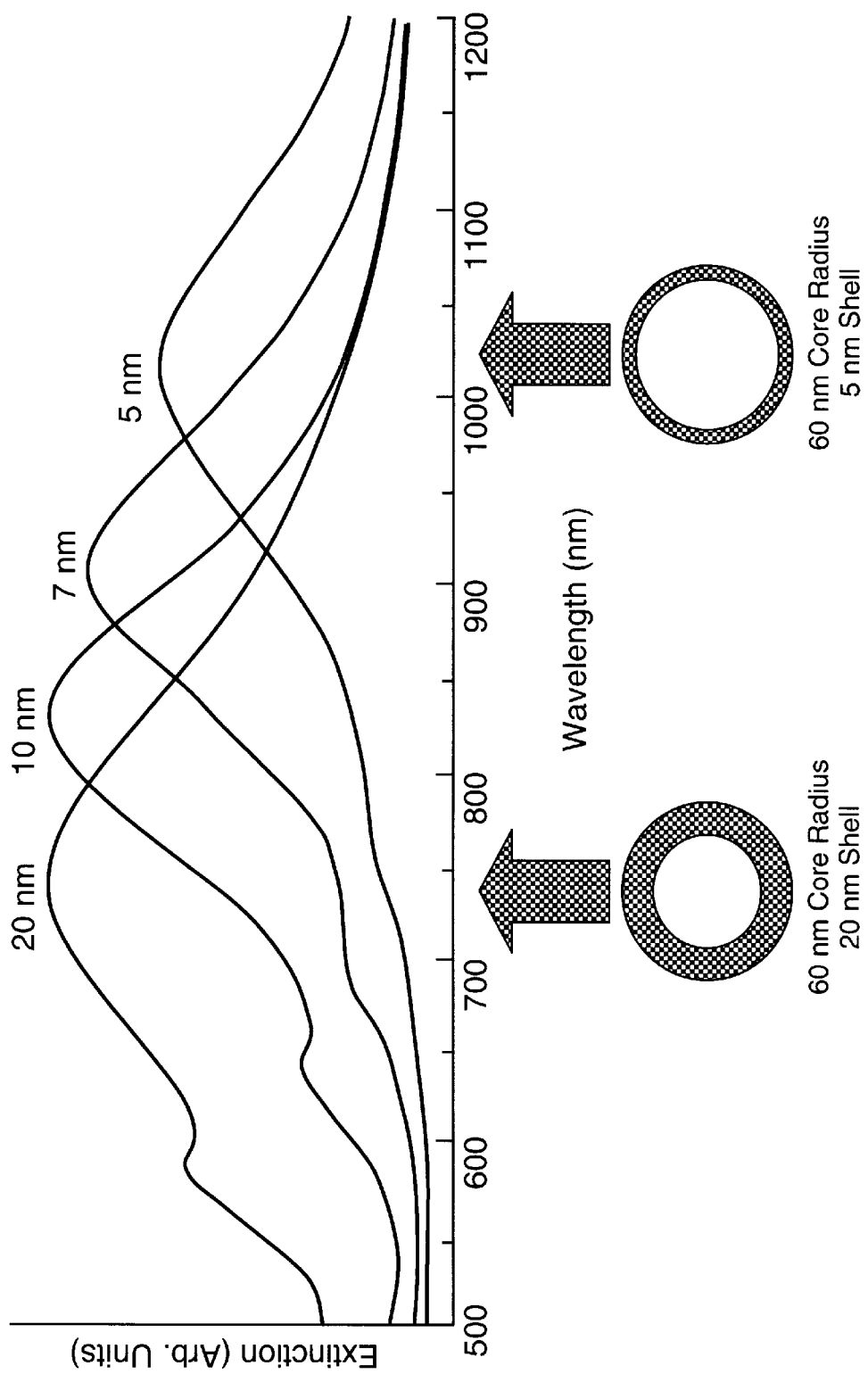
FIG. 1 is a graph of the optical resonances (extinction, arbitrary units) of gold shell-silica core nanoshells, as a function of their core/shell ratio—with arrows indicating values for nanoshells with 60 nm core radii and 20 versus 5 nm shell thickness.

It is readily apparent to one skilled in the art that various embodiments and modifications may be made to the invention disclosed in this Application without departing from the scope and spirit of the invention.

As used herein the specification, "a" or "an" may mean one or more. As used herein in the claim(s), when used in conjunction with the word "comprising", the words "a" or "an" may mean one or more than one. As used herein "another" may mean at least a second or more.

The terms "cell," "cell line," and "cell culture" as used herein may be used interchangeably. All of these terms also include their progeny, which are any and all subsequent generations. It is understood that all progeny may not be identical due to deliberate or inadvertent mutations.

The term "targeted" as used herein encompasses the use of antigen-antibody binding, ligand-receptor binding, and other chemical binding interactions, as well as non-chemical means such as direct injection.

As used herein, "energy source" encompasses any and all forms of excitation, including radiation from any or all regions of the electromagnetic spectrum, ultrasound, magnetic fields, electric fields, microwave radiation, laser excitation, etc.

As used herein, "light" means electromagnetic radiation.

As used herein, "electromagnetic radiation" is defined as radiation having an electric field and a magnetic field propagating at right angles to one another and is further limited to only the following: microwaves, infrared, visible, ultraviolet, x-rays, gamma rays, and cosmic rays. As used herein, "electromagnetic radiation" does not include radio-frequency radiation.

As used herein, "non-cellular non-tissue material" is any biological material other than cells and tissue and may include plaque, virus material, etc.

As used herein "delivering" nanoparticles to a location is defined as effecting the placement of the nanoparticles attached to, next to, or sufficiently close to the location such that any heat generated by the nanoparticles is transferred to the location and any imaging of the local environment by the nanoparticles includes imaging of the desired location.

As used herein, "illuminate" is defined as shedding electromagnetic radiation or other energy sources in such a way as to resolve or to otherwise differentiate an object from adjacent objects or to resolve distinct regions within one object.

As used herein, "nanoparticle" is defined as a particle having a diameter of from 1 to 1000 nanometers, having any size, shape or morphology. As used herein, "nanoshell" is a nanoparticle having a discrete dielectric or semiconducting core section surrounded by one or more conducting shell layers. A "nanoshell" is a subspecies of nanoparticles characterized by the discrete core/shell structure. Both nanoshells and nanoparticles may contain dopants such as $Pr^{+3}$, $Er^{+3}$, and $Nd^{+3}$.

As used herein, "nanoparticle" means one or more nanoparticles. As used herein, "nanoshell" means one or more nanoshells. As used herein, "shell" means one or more shells.

The term "tumor" as used herein includes any swelling or tumefaction. As used herein, tumor also refers to a neoplasm.

The term "benign tumor" as used herein is defined as a tumor does not form metastases and does not invade or destroy adjacent tissue. The term "malignant tumor" as used herein is defined as a tumor that invades surrounding tissues, is usually capable of producing metastases, may recur after attempted removal.

The term "cancer" as used herein is defined as a general variety of malignant neoplasms. Cancer herein is interchangeable with carcinoma and sarcoma.

The term "antibody" as used herein, refers to an immunoglobulin molecule, which is able to specifically bind to a specific epitope on an antigen. As used herein, an antibody is intended to refer broadly to any immunologic binding agent such as IgG, IgM, IgA, IgD and IgE. Antibodies can be intact immunoglobulins derived from natural sources or from recombinant sources and can be immunoactive portions of intact immunoglobulins. Antibodies are typically tetramers of immunoglobulin molecules. The antibodies in the present invention may exist in a variety of forms including, for example, polyclonal antibodies, monoclonal antibodies, Fv, Fab and $F(ab)_2$, as well as single chain antibodies and humanized antibodies (Harlow et al., 1988; Houston et al., 1988; Bird et al., 1988).

As used herein, "coupling" refers to any chemical association and includes both covalent and non-covalent interactions.

The term "autoimmune disease" as used herein is defined as a disorder that results from autoimmune responses. Autoimmunity is an inappropriate and excessive response to self-antigens. Examples include but are not limited to, Addision's disease, Graves' disease, multiple sclerosis, myxedema, pernicious anemia, rheumatic fever, rheumatoid arthritis, systemic lupus erythematosus, and ulcerative colitis.

The term "inflammation" as used herein, is a general term for the local accumulation of fluid, plasma proteins, and white blood cells that is initiated by physical injury, infection or a local immune response. This is also known as an inflammatory response. The cells that invade tissue undergoing inflammatory responses are often called inflammatory cells or an inflammatory infiltrate.

Herein, the abbreviation "IR" means infrared, the abbreviation "UV" means ultraviolet, and the abbreviation "VIS" means visible.

As used herein, "localized" means substantially limited to a desired area with only minimal, if any, dissemination outside of such area.

In an important embodiment of the present invention, the nanoparticles administered to an animal using standard methods. Animals that may be treated using the method of the invention include, but are not limited to humans, cows, horses, pigs, dogs, cats, sheep goats, rabbits, rats, mice, birds, chickens or fish.

A method to selectively image or kill cells and/or tissue for diagnostic and therapeutic applications has been developed. The particles are ideally of nanometer-scale dimensions. The method may include targeting schemes involving specific chemical interactions (e.g., antigen-antibody binding, etc.) or may consist of the simple delivery of the therapeutic reagents to the desired area. The direction or targeting of the therapy may be to the surface of the subject cells and/or tissue, or it may be to other, interior sites. Several new classes of such nanoparticles that offer more specific and accurate imaging technologies, based on nanoparticles that emit or scatter near infrared light and that can be easily conjugated to antibodies, as well as highly localized, targeted, and minimally invasive treatment strategies based on photothermal interactions with nanoparticles, have been developed. In a preferred embodiment to kill the targeted cells, the nanoparticles are nanoshells and are formed with a core of a dielectric or inert material such as silicon, coated with a material such as a highly conductive metal which can be excited using radiation such as near infrared light (approximately 800 to 1300 nm). Upon excitation, the nanoshells emit heat. The combined diameter of the shell and core of the nanoshells ranges from the tens to the hundreds of nanometers.

Importantly, in all embodiments of the present invention, the excitation may be effected from an excitation source inside the material to which hyperthermia is to be induced or it may be effected by an excitation source outside the material. In the in vivo applications, it may be effected by an excitation source inside the body or outside the body. In in vivo applications wherein the excitation source is inside the body, the excitation source may be in the subject material or outside it.

Near infrared light is advantageous for its ability to penetrate tissue. Other types of radiation can also be used, depending on the selection of the nanoparticle coating and targeted cells. Examples include x-rays, magnetic fields, electric fields, and ultrasound. The problems with the existing methods for hyperthermia, especially for use in cancer therapy, such as the use of heated probes, microwaves, ultrasound, lasers, perfusion, radiofrequency energy, and radiant heating is avoided since the levels of radiation used as described herein is insufficient to induce hyperthermia except at the surface of the nanoparticles, where the energy is more effectively concentrated by the metal surface on the dielectric. The particles can also be used to enhance imaging, especially using infrared diffuse photon imaging methods. Targeting molecules can be antibodies or fragments thereof, ligands for specific receptors, or other proteins specifically binding to the surface of the cells to be targeted.

Materials and methods are described to deliver nanoparticles that scatter, absorb, and/or emit near infrared light to cells; to use these as contrast agents or emitters to optically tag cells for near-IR imaging; to provide infrared tomographic imaging methods based on these specifically tagged cells and to photothermally target the destruction of individual cells by optically exciting the nanoparticle tags with near infrared light.

Metal Nanoshells

Metal nanoshells are a type of nanoparticle composed of a dielectric (for instance, silica) core coated with one or more metallic (for instance, gold) layers. The shell layer is formed of a metal or metal-like material that preferably conducts electricity, although materials with sufficiently lower dielectric constants than the core material can also be used. Preferred metals include gold, silver, copper, platinum, palladium, lead, and iron. Gold is most preferred. Gold nanoshells possess physical properties similar to gold colloid, in particular, a strong optical absorption due to the collective electronic response of the metal to light. The optical absorption of gold colloid yields a brilliant red color which has been of considerable utility in consumer-related medical products, such as home pregnancy tests. In contrast, the optical response of gold nanoshells depends dramatically on the relative size of the nanoparticle core and the thickness of the gold shell (Neeves & Birnboim, 1989; Kreibig and Vollmer, 1995). By varying the relative core and shell thicknesses, the color of gold nanoshells can be varied across a broad range of the optical spectrum that spans the visible and the near infrared spectral regions.

Figure 2:
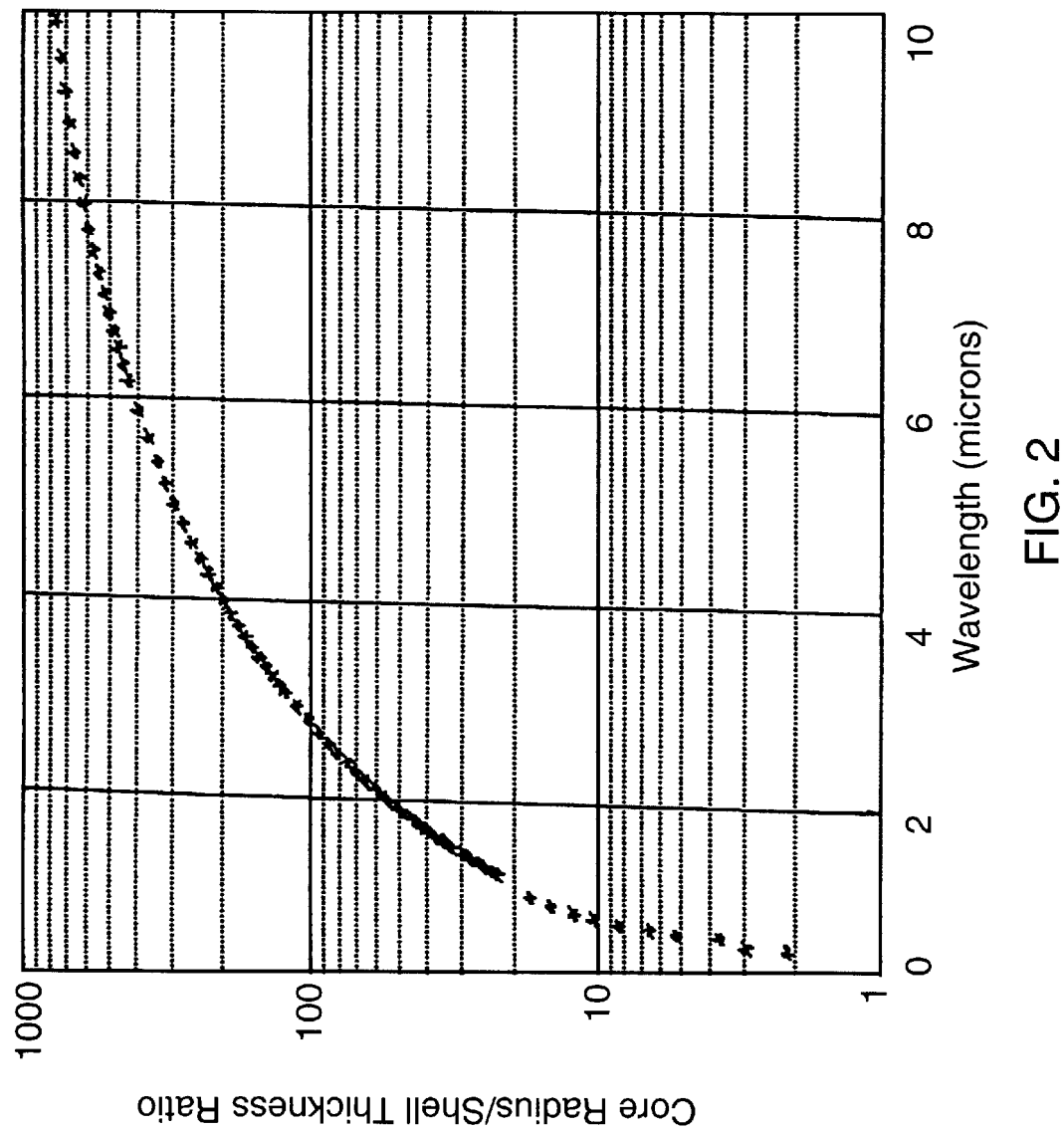
FIG. 2 is a graph of the core/shell ratio as a function of a resonance wavelength (microns) for gold/silica nanoshells.

Gold nanoshells can be made to either preferentially absorb or scatter light by varying the size of the particle relative to the wavelength of the light at their optical resonance. In FIG. 1, a Mie scattering plot of the nanoshell plasmon resonance wavelength shift as a function of nanoshell composition for the case of a 40 nm gold/silica nanoshell is depicted. In this figure, the core and shall of the nanoparticles are depicted to relative scale directly beneath their corresponding optical resonances. In FIG. 2, a plot of the core/shell ratio versus resonance wavelength for a silica core/gold shell nanoparticle is displayed. The extremely agile "tunability" of the optical resonance is a property completely unique to metal nanoshells: in no other molecular or nanoparticle structure can the resonance of the optical absorption properties be systematically "designed", let alone so easily and over such an enormous range of wavelengths.

Other materials may also be used. Organic conducting materials such as polyacetylene and doped polyanaline can also be used. Additional layers, such as a non-conducting layer, a conducting layer, or a sequence of such layers, such as an alternating sequence of conducting and non-conducting layers, can be bound to the shell layer. The core should be non-conducting, for example, formed of a dielectric material or semiconductor material. Examples include silicon dioxide, titanium dioxide, polymethyl methacrylate (PMMA), polystyrene, gold sulfide, and macromolecules such as dendrimers. Exemplary semiconductive materials include CdSe, CdS, and GaAs. The nature of the material affects the properties of the particles. For example, if the dielectric constant of the shell layer is larger relative to a particle having a core with a given dielectric constant, the absorbance maximum of the particle will be blue-shifted relative to a particle having a core with a lower dielectric constant. The preferred core material is colloidal silica, which can be prepared by base catalyzed reaction of tetraalkoxysilanes.

The shell layer and core can be linked, for example, through ionic bonds, lone-pair interactions, hydrogen bonds, or Van der Waals interaction. An exemplary linker is aminopropyltriethoxysilane.

In the typical embodiment, the particles are not biodegradable but will tend to be cleared following administration by the reticuloendothelial system (RES). However, in some embodiments, it may be desirable to link the core, the metal shell or an intervening layer, using biodegradable materials such as a polyhydroxy acid polymer which degrades hydrolytically in the body so that removal of the particles after a period of time is facilitated.

In the preferred embodiment, the particles are homogeneous in size distribution and shape. Although described herein with reference to spherical particles, other shapes can be fabricated using the same methods. Examples are irregular particles, cylinders, disks, and other geometric shapes.

Typically, the radius will be between one and ten nanometers. However, cores can range from 10 nm to greater than four microns and shell layers can range from one to 100 nm in thickness.

A comprehensive investigation of the optical properties of metal nanoshells is reported by Averitt et al., 1997 as well as Averitt et al., 1999. Quantitative agreement between Mie scattering theory and the experimentally observed optical resonant properties has been achieved. Based on this success, it is now possible to predictively design gold nanoshells with the desired optical resonant properties, and then to fabricate the nanoshell with the dimensions and nanoscale tolerances necessary to achieve these properties (Oldenburg et al. 1998).

Preparation and Photophysical Properties of Metal Nanoshells

The synthetic protocol for the fabrication of gold nanoshells is based on the well-known principles of molecular self-assembly and colloid chemistry in aqueous solution. The method is straightforward in concept 1. Grow or obtain silica nanoparticles dispersed in solution, for example, the silicone dioxide particles such as LUDOX TM-50 colloidal silica particles available from Aldrich Chemical Co., Milwaukee, Wis.
2. Attach very small (1–2 nm) metal "seed" colloid to the surface of the nanoparticles via molecular linkages; these seed colloids cover the dielectric nanoparticle surfaces with a discontinuous metal colloid layer,
3. Grow additional metal onto the "seed" metal colloid adsorbates via chemical reduction in solution.

Figure 3A:
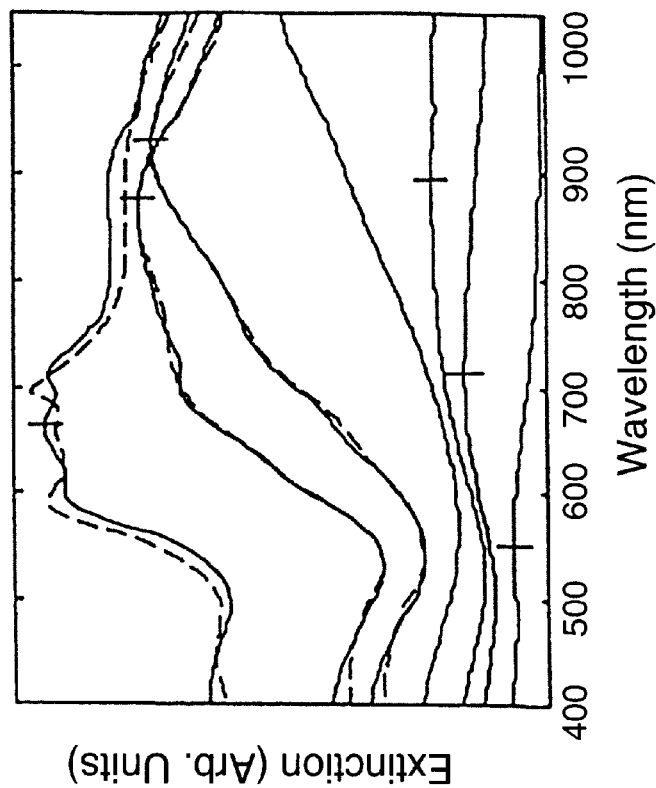
FIGS. 3a and 3b are plots of extinction (arbitrary units) versus wavelength (nm) for growth of gold shell on 120 nm (FIG. 3a) and 340 nm (FIG. 3b) diameter silica nanoparticle. The lower spectral curves follow the evolution of the optical absorption as coalescence of the gold layer progresses. Once the shell is complete, the peak absorbance is shifted to shorter wavelengths. Corresponding theoretical peaks are plotted with dashed lines. The peak shifts are more pronounced with only the shoulder of the middle curve visible in the instrument range for the larger shell thickness.
Figure 3B:
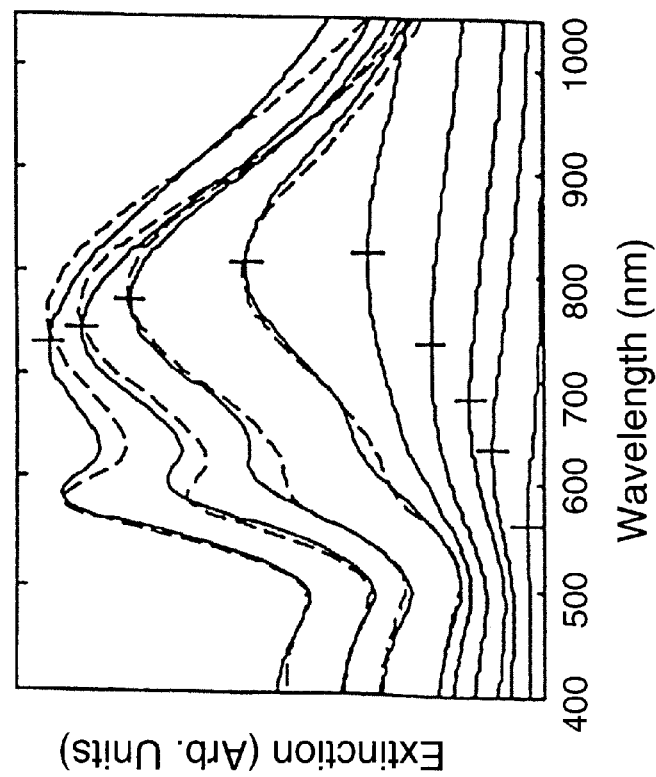

Tethered clusters of metals, ions or atoms are linked to the core particle through a linker molecule. In general, metal is deposited onto the tethered clusters until a coherent metal shell of the desired thickness is formed. This may be by reduction of solution metal or by a colloid-based deposition process. Deposition can be initiated or driven photochemically. This approach has been used to grow both gold and silver metallic shells onto silica nanoparticles. FIGS. 3a and 3b show the optical signature of nanoshell coalescence and growth for two different nanoshell core diameters.

For any given particle, the maximum absorbance depends upon the ratio of the thickness of the non-conducting layer to the conducting shell layer. The spectral location of the maximum of the plasmon resonance peak depends upon the ratio of the core radius to shell thickness, as well as the dielectric functions of the core and shell. The presence of a dielectric core shifts the plasmon resonance to longer wavelengths relative to a solid nanoparticle made exclusively of the metallic shell material. For a given core radius, a thin shell will have a plasmon peak that is shifted to longer wavelengths relative to a thicker shell. Metal nanoshells offer resonance tunability that solid nanoparticles lack.

Based on the core/shell ratios that can be achieved with this protocol, gold nanoshells with optical resonances extending from the visible region to approximately 3 microns in the infrared can be fabricated. This spectral region includes the 800–1300 nm and 1600–1850 nm "water windows" of the near infrared, a region of high physiological transmissivity which has been demonstrated as the spectral region best suited for optical bio-imaging and biosensing applications.

The optical properties of gold nanoshells, when coupled with their biocompatibility and their ease of bioconjugation, render these nanoparticles ideal for targeted bioimaging and therapeutics applications.

Rare Earth Nanoemitters

A method of incorporating emissive rare earth (lanthanide) ionic species into silica nanoparticles has been developed. Rare earth ions such as Neodymium, Erbium, and Praseodymium are robust infrared fluorophores and are used extensively as gain media in commercial near infrared solid state lasers and amplifiers. The rare earth fluorophores that have been successfully incorporated into silica nanoparticles are shown in Table 1. For several of these ionic species, both excitation and emission wavelengths lie in the "water window" of the near infrared, a region of high light transmission through tissue, which will facilitate in vivo applications.

TABLE 1

Rare earth ionic species that have been incorporated into nanoparticles, and their (selected) corresponding excitation and emission wavelengths.

| Dopant | Excitation Wavelength (nm) | Emission Wavelength (nm) |
| --- | --- | --- |
| $Pr^{3+}$ | 488, 1020 | 580–750, 1260–1350 |
| $Er^{3+}$ | 980, 1480 | 980–1000, 1500–1600 |
| $Nd^{3+}$ | 795 | 900–950, 100–1150, 1320–1400 |

The rare earth doped silica nanoparticles should show universal utility as infrared fluorophores in bioimaging applications. The surfaces of these silica nanoparticles can be functionalized and terminated in a variety of ways, including amination or the growth of a gold shell layer, to facilitate antibody conjugation for the targeted applications.

Figure 4:
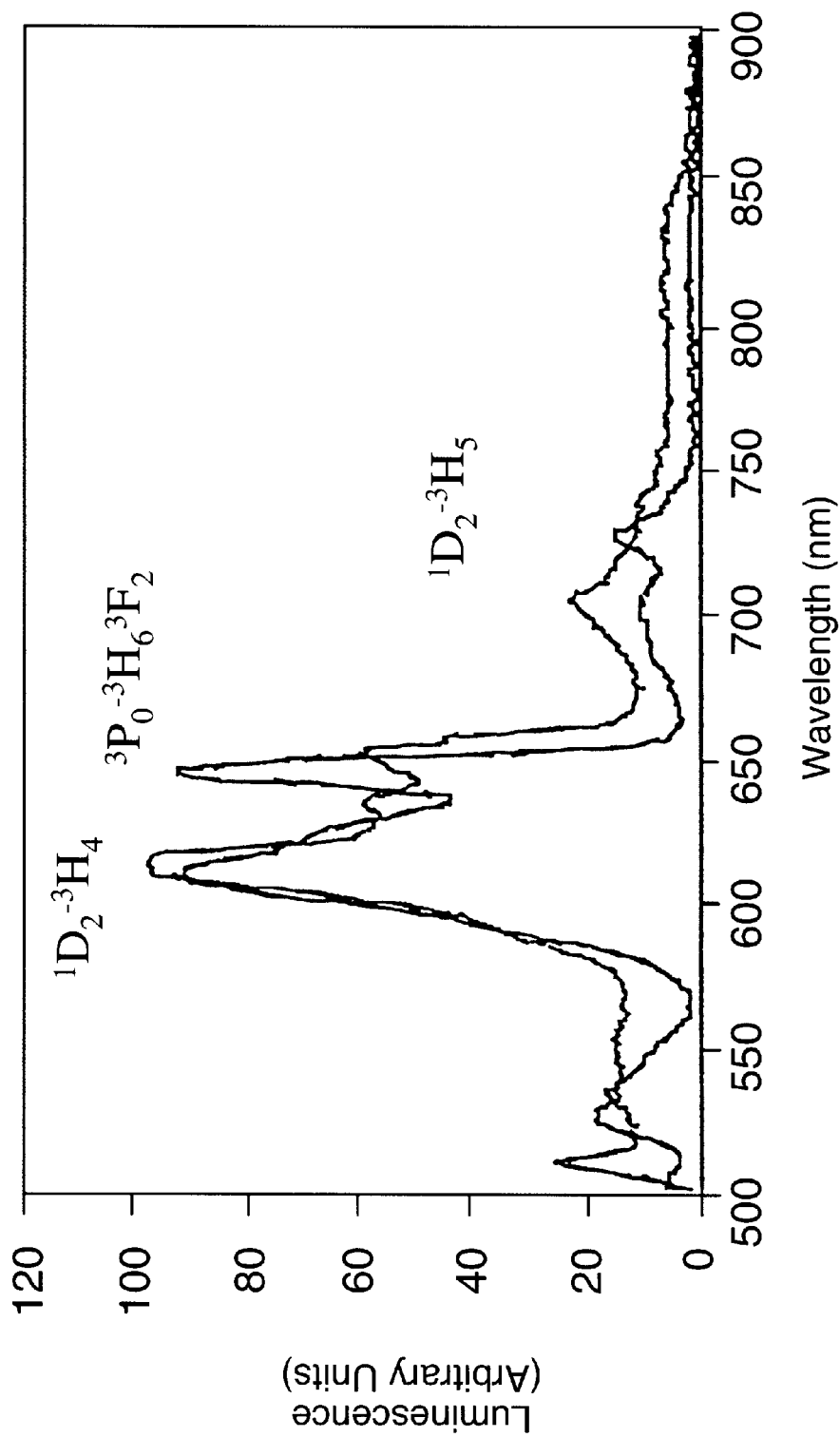
FIG. 4 is a graph of the luminescence (arbitrary units) spectrum (visible region) of $Pr^{+3}$ ions incorporated into silica nanoparticles. Nanoparticle emission; bulk $Pr^{3+}$:silica emission.

Rare earth incorporation is achieved by modifying the silica nanoparticle synthesis from basic to acidic conditions, under which the rare earth ions remain soluble and thus can be incorporated into the nanoparticle as it grows. The nanoparticles formed are highly spherical and range in size from approximately 100 nm to greater than 2 microns. Monodisperse distributions of these nanoparticles have also been achieved. Bright room temperature fluorescence has been achieved for all rare earth species that have been incorporated into the nanoparticle matrices. A typical visible-region fluorescence spectrum of $Pr^{3+}$, shown in comparison to $Pr^{3+}$ emission in bulk silica prepared by the standard high-temperature diffusion process, is shown in FIG. 4.

It should be emphasized that the rare earth nanoemitters can be nanoparticles lacking a shell layer, or alternatively they may take the form of nanoshells having a core material and one or more shell layers. The rare earth-doped section is typically the core, but it may exist in a shell layer.

Heat Transfer in Nanoshell-Polymer Composites

Figures 5A, 5B:
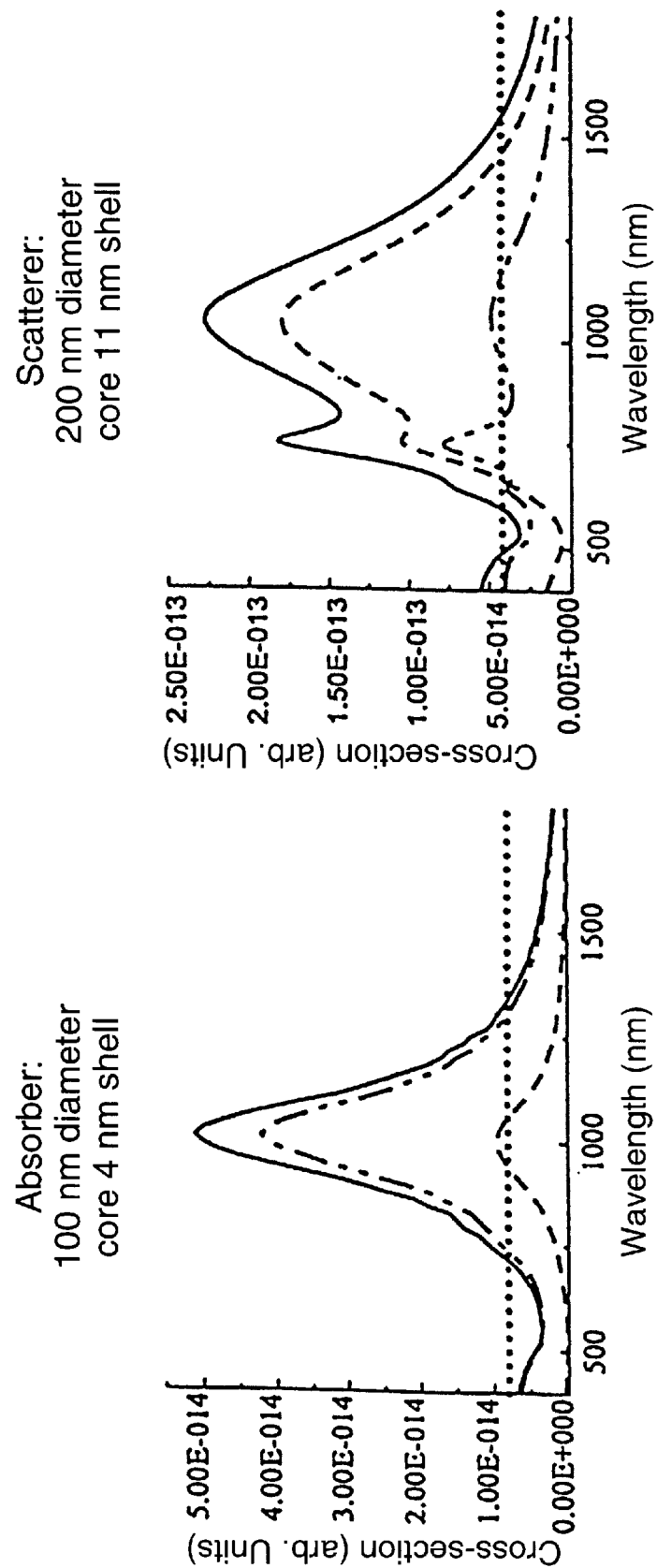
FIGS. 5a and 5b are graphs of the cross section (arbitrary units) versus wavelength (nm) showing total extinction, absorption and scattering at 1000 nm for gold nanoshells of dimension (a) 100 nm diameter core, 4 nm shell; (b) 200 nm diameter core, 11 nm shell.

By varying the size of gold nanoshells relative to their resonance wavelength, nanoshells can be selectively made to be either predominantly absorptive or predominantly scattering of resonant light. This is illustrated in FIG. 5 for a nanoshell resonant at a wavelength of 1000 nm. At laser intensities typical for biological imaging, both scatterers and absorbers should prove to be of utility in enhancing the contrast and resolution of targeted structures in biological tissue, providing a means to selectively increase the absorption or scattering coefficient of the targeted structure in the tissue.

Figure 6:
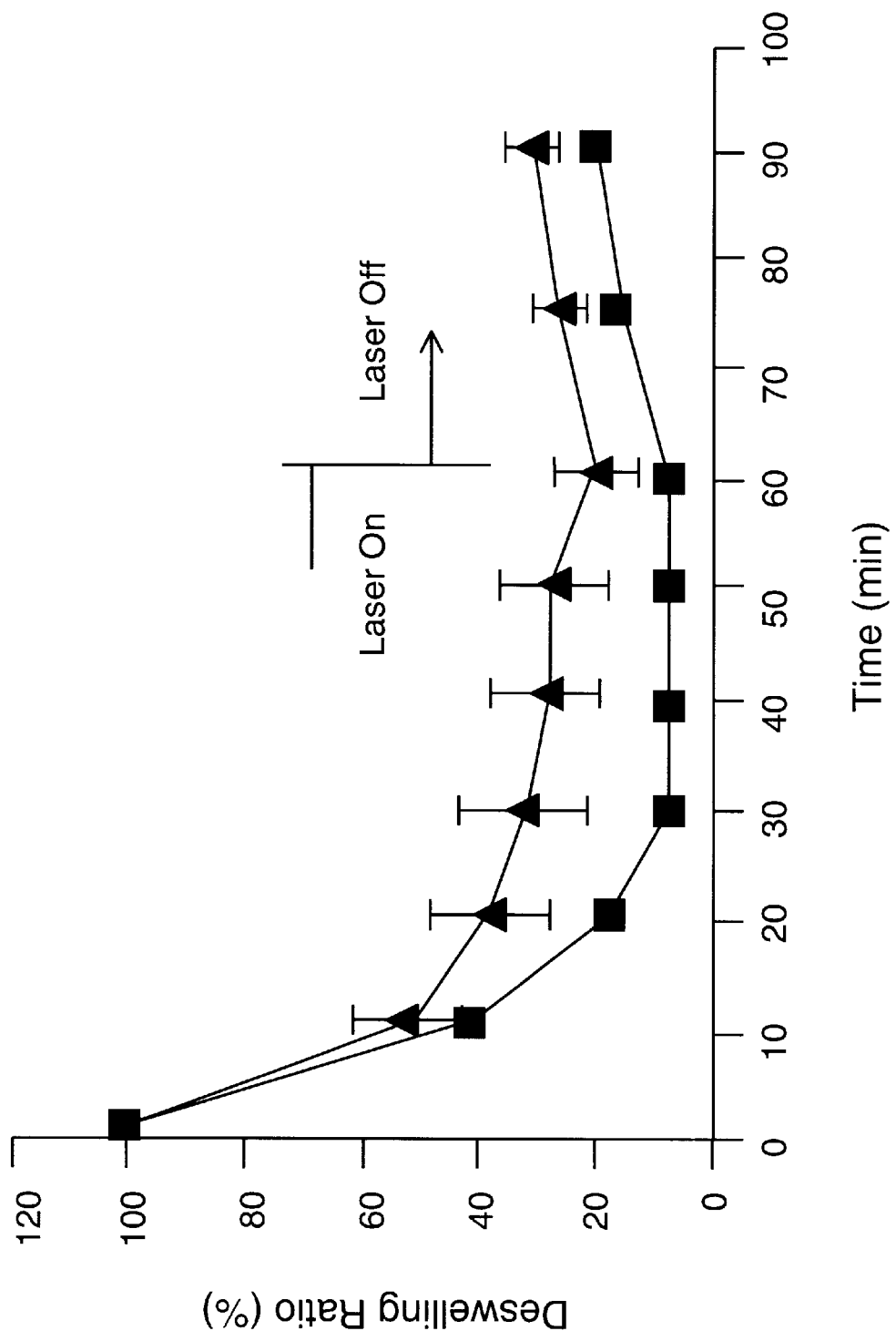
FIG. 6 is a plot of collapse and swelling of NIPAAm-co-AAm hydrogels (diamonds) and nanoshell composite hydrogels (squares), during and after irradiation with a Nd:YAG laser at 1064 nm (164 mJ/pulse, 7 ns pulse length, 10 Hz repetition rate).

Metal nanoshells are not as susceptible to photobleaching or photoinduced damage than are typical molecular fluorophores. Since the nanoshell resonance decays nonradiatively (with typical quantum efficiencies of a few percent), most of the energy due to optical absorption is converted into heat. Thus resonant illumination of highly absorptive metal nanoshells can provide significant local heating to the microscopic environment of the nanoshells. We have recently demonstrated that this effect can be used to provide significant heat transfer to induce a phase transition when raised above its lower critical solution temperature (LCST), nominally 45° C. (Sershen et al., 1999). When hydrogels of the copolymer N-isopropyl-acrylamide-co-acrylamide (NIPAAm-co-AAm) are doped either homogeneously or heterogeneously with absorptive gold nanoshells, the deswelling transition is induced by irradiation with light at the nanoshell resonance wavelength (FIG. 6). This observation was verified against a control sample of copolymer without nanoshells, to confirm that the weak residual absorption of the copolymer at the irradiation wavelength was insufficient to induce a temperature rise and the resultant deswelling transition. This local heating effect can be observed at relatively modes power levels using either continuous or pulsed laser sources, at power levels significantly less intense than those used in bioimaging applications. Photoinduced local heating of nanoshell-conjugated antibodies targeted to tumor cells, a procedure that should lead to local, specific cell death, is the focus of the therapeutics section of this proposal.

Production of Antibodies

The term antibody is used to refer to any antibody-like molecule that has an antigen binding region, and includes antibody fragments such as Fab', Fab, F(ab')2, single domain antibodies (DABs), Fv, scFv (single chain Fv), and the like. The techniques for preparing and using various antibody-based constructs and fragments are well known in the art. Means for preparing and characterizing antibodies are also well known in the art (See, e.g., *Antibodies: A Laboratory Manual,* Cold Spring Harbor Laboratory, 1988; incorporated herein by reference).

Monoclonal antibodies (MAbs) are recognized to have certain advantages, e.g., reproducibility and large-scale production, and their use is generally preferred. The invention thus provides antibodies of the human, murine, monkey, rat, hamster, rabbit and chicken origin.

However, humanized antibodies are also contemplated, as are chimeric antibodies from mouse, rat, or other species, bearing human constant and/or variable region domains, bispecific antibodies, recombinant and engineered antibodies and fragments thereof. Methods for the development of antibodies that are "custom-tailored" to the patient's disease are likewise known and such custom-tailored antibodies are also contemplated.

Antibodies may be further purified, if desired, using filtration, centrifugation and various chromatographic methods such as HPLC or affinity chromatography. Fragments of the antibodies of the invention can be obtained from the antibodies so produced by methods which include digestion with enzymes, such as pepsin or papain, and/or by cleavage of disulfide bonds by chemical reduction. Alternatively, antibody fragments encompassed by the present invention can be synthesized using an automated peptide synthesizer or by expression of full-length gene or gene fragments in *E. coli.*

It is also contemplated that a molecular cloning approach may be used to generate monoclonal antibodies. In one embodiment, combinatorial immunoglobulin phagemid libraries are prepared from RNA isolated from the spleen of the immunized animal, and phagemids expressing appropriate antibodies are selected by panning using cells expressing the antigen and control cells. The advantages of this approach over conventional hybridoma techniques are that approximately $10^4$ times as many antibodies can be produced and screened in a single round, and that new specificities are generated by H and L chain combination which further increases the chance of finding appropriate antibodies.

Conjugation of Antibodies to Reporter Molecules

In order to increase the efficacy of antibody molecules as diagnostic or therapeutic agents, it is conventional to link or covalently bind or complex at least one desired molecule or moiety. Such a molecule or moiety may be, but is not limited to, at least one effector or reporter molecule. Effector molecules comprise molecules having a desired activity, e.g., cytotoxic activity. In addition to the nanoshells of the present invention other examples of effector molecules which can be attached to antibodies include, but are not limited to toxins, anti-tumor agents, therapeutic enzymes, radio-labeled nucleotides, antiviral agents, chelating agents, cytokines, growth factors, and oligo- or poly-nucleotides. A reporter molecule is defined as any moiety which may be detected using an assay. Non-limiting examples of reporter molecules which have been conjugated to antibodies include enzymes, radiolabels, haptens, fluorescent labels, phosphorescent molecules, chemiluminescent molecules, chromophores, luminescent molecules, photoaffinity molecules, colored particles or ligands, such as biotin.

In order to detect the amount of antibodies conjugated to the present invention, several immunodetection methods can be used. For example, some immunodetection methods include, but are not limited to enzyme linked immunosorbent assay (ELISA), radioimmunoassay (RIA), immunoradiometric assay, fluoroimmunoassay, chemiluminescent assay, bioluminescent assay, and Western blot to mention a few. The steps of various useful immunodetection methods have been described in the scientific literature, such as, e.g., Doolittle MH and Ben-Zeev O, 1999; Gulbis B and Galand P, 1993; De Jager R et al., 1993; and Nakamura et al., 1987, each incorporated herein by reference.

Nanoshell and Nanoemitter Conjugated Antibodies

Because the metal layer of gold nanoshells is grown using the same chemical reaction as gold colloid synthesis, the surfaces of gold nanoshells are virtually chemically identical to the surfaces of the gold nanoparticles universally used in bioconjugate applications. The use of gold colloid in biological applications began in 1971, when Faulk and Taylor invented immunogold staining.

The synthesis of the rare earth doped nanoparticles proceeds very similarly to the synthesis of the silica nanoparticles used as nanoshell cores. Following nanoparticle synthesis, the surface is composed of hydroxyl groups. These particles may be subsequently aminated via reaction with aminopropyltriethoxysilane, thus allowing several options for antibody conjugation. In some instances, metal shells may be grown on these doped nanoparticles, thus creating structures with both emissive and scattering characteristics. Shell growth and subsequent attachment of antibodies to the gold colloid layer can proceed as described herein. Alternatively, antibodies can be covalently immobilized to either hydroxylated or aminated nanoparticle surfaces via a variety of chemical schemes, including carbodiimide chemistry, diisocyanate linkers, succinimidyl esters, etc. In addition, antibodies can be immobilized via polymer tethering chains. This can be accomplished with difunctional polyethylene glycol derivatives. This immobilization scheme may increase the biological activity of the immobilized antibodies by enhancing their mobility and thus their ability to interact with their target ligand. Efficiency of antibody immobilization can be determined with horseradish peroxidase (HRP) labeled antibodies. Activity of the nanoparticle-conjugated antibodies can be assessed with HRP labeled antigens and by examining nanoparticle binding to antigen coated surfaces. Nanoparticle binding to these surfaces can be quantitatively assessed by atomic force microscopy (AFM) and fluorescence. Results can be compared to ELISA measurements of the antigen surface concentration.

Pharmaceutical Compositions

Aqueous compositions of the present invention comprise an effective amount of the nanoshell or chemical composition of the present invention dissolved and/or dispersed in a pharmaceutically acceptable carrier and/or aqueous medium.

The phrases pharmaceutically and/or pharmacologically acceptable refer to molecular entities and/or compositions that do not produce an adverse, allergic and/or other untoward reaction when administered to an animal, as appropriate.

As used herein, pharmaceutically acceptable carrier includes any and/or all solvents, dispersion media, coatings, antibacterial and/or antifungal agents, isotonic and/or absorption delaying agents and/or the like. The use of such media and/or agents for pharmaceutical active substances is well known in the art. Except insofar as any conventional media and/or agent is incompatible with the active ingredient, its use in the therapeutic compositions is contemplated. Supplementary active ingredients can also be incorporated into the compositions. For administration, preparations should meet sterility, pyrogenicity, general safety and/or purity standards as required by FDA Office of Biologics standards.

The biological material should be extensively dialyzed to remove undesired small molecular weight molecules and/or lyophilized for more ready formulation into a desired vehicle, where appropriate. The active compounds may generally be formulated for parenteral administration, e.g., formulated for injection via the intravenous, intramuscular, sub-cutaneous, intralesional, and/or even intraperitoneal routes. The preparation of an aqueous compositions that contain an effective amount of the nanoshell composition as an active component and/or ingredient will be known to those of skill in the art in light of the present disclosure. Typically, such compositions can be prepared as injectables, either as liquid solutions and/or suspensions; solid forms suitable for using to prepare solutions and/or suspensions upon the addition of a liquid prior to injection can also be prepared; and/or the preparations can also be emulsified.

The pharmaceutical forms suitable for injectable use include sterile aqueous solutions and/or dispersions; formulations including sesame oil, peanut oil and/or aqueous propylene glycol; and/or sterile powders for the extemporaneous preparation of sterile injectable solutions and/or dispersions. In all cases the form must be sterile and/or must be fluid to the extent that easy syringability exists. It must be stable under the conditions of manufacture and/or storage and/or must be preserved against the contaminating action of microorganisms, such as bacteria and/or fungi.

Solutions of the active compounds as free base and/or pharmacologically acceptable salts can be prepared in water suitably mixed with a surfactant, such as hydroxypropylcellulose. Dispersions can also be prepared in glycerol, liquid polyethylene glycols, and/or mixtures thereof and/or in oils. Under ordinary conditions of storage and/or use, these preparations contain a preservative to prevent the growth of microorganisms.

The nanoshell composition of the present invention can be formulated into a composition in a neutral and/or salt form. Pharmaceutically acceptable salts, include the acid addition salts (formed with the free amino groups of the protein) and/or which are formed with inorganic acids such as, for example, hydrochloric and/or phosphoric acids, and/or such organic acids as acetic, oxalic, tartaric, mandelic, and/or the like. Salts formed with the free carboxyl groups can also be derived from inorganic bases such as, for example, sodium, potassium, ammonium, calcium, and/or ferric hydroxides, and/or such organic bases as isopropylamine, trimethylamine, histidine, procaine and/or the like.

The carrier can also be a solvent and/or dispersion medium containing, for example, water, ethanol, polyol (for example, glycerol, propylene glycol, and/or liquid polyethylene glycol, and/or the like), suitable mixtures thereof, and/or vegetable oils. The proper fluidity can be maintained, for example, by the use of a coating, such as lecithin, by the maintenance of the required particle size in the case of dispersion and/or by the use of surfactants. The prevention of the action of microorganisms can be brought about by various antibacterial and/or antifungal agents, for example, parabens, chlorobutanol, phenol, sorbic acid, thimerosal, and/or the like. In many cases, it will be preferable to include isotonic agents, for example, sugars and/or sodium chloride. Prolonged absorption of the injectable compositions can be brought about by the use in the compositions of agents delaying absorption, for example, aluminum monostearate and/or gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and/or the required other ingredients from those enumerated above. In the case of sterile powders for the preparation of sterile injectable solutions, the preferred methods of preparation are vacuum-drying and/or freeze-drying techniques which yield a powder of the active ingredient plus any additional desired ingredient from a previously sterile-filtered solution thereof The preparation of more, and/or highly, concentrated solutions for direct injection is also contemplated, where the use of DMSO as solvent is envisioned to result in extremely rapid penetration, delivering high concentrations of the active agents to a small tumor area.

Upon formulation, solutions will be administered in a manner compatible with the dosage formulation and/or in such amount as is therapeutically effective. The formulations are easily administered in a variety of dosage forms, such as the type of injectable solutions described above, but drug release capsules and/or the like can also be employed.

For parenteral administration in an aqueous solution, for example, the solution should be suitably buffered if necessary and/or the liquid diluent first rendered isotonic with sufficient saline and/or glucose. These particular aqueous solutions are especially suitable for intravenous, intramuscular, subcutaneous and/or intraperitoneal administration. In this connection, sterile aqueous media which can be employed will be known to those of skill in the art in light of the present disclosure. For example, one dosage could be dissolved in 1 ml of isotonic NaCl solution and/or either added to 1000 ml of hypodermoclysis fluid and/or injected at the proposed site of infusion, (see for example, "Remington's Pharmaceutical Sciences" 15th Edition, pages 1035–1038 and/or 1570–1580). Some variation in dosage will necessarily occur depending on the condition of the subject being treated. The person responsible for administration will, in any event, determine the appropriate dose for the individual subject.

In addition to the compounds formulated for parenteral administration, such as intravenous and/or intramuscular injection, other pharmaceutically acceptable forms include, e.g., tablets and/or other solids for oral administration; liposomal formulations; time release capsules; and/or any other form currently used, including cremes.

One may also use nasal solutions and/or sprays, aerosols and/or inhalants in the present invention. Nasal solutions are usually aqueous solutions designed to be administered to the nasal passages in drops and/or sprays. Nasal solutions are prepared so that they are similar in many respects to nasal secretions, so that normal ciliary action is maintained. Thus, the aqueous nasal solutions usually are isotonic and/or slightly buffered to maintain a pH of 5.5 to 6.5. In addition, antimicrobial preservatives, similar to those used in ophthalmic preparations, and/or appropriate drug stabilizers, if required, may be included in the formulation.

Additional formulations which are suitable for other modes of administration include vaginal suppositories and/or pessaries. A rectal pessary and/or suppository may also be used. Suppositories are solid dosage forms of various weights and/or shapes, usually medicated, for insertion into the rectum, vagina and/or the urethra. After insertion, suppositories soften, melt and/or dissolve in the cavity fluids. In general, for suppositories, traditional binders and/or carriers may include, for example, polyalkylene glycols and/or triglycerides; such suppositories may be formed from mixtures containing the active ingredient in the range of 0.5% to 10%, preferably 1%–2%.

Oral formulations include such normally employed excipients as, for example, pharmaceutical grades of mannitol, lactose, starch, magnesium stearate, sodium saccharine, cellulose, magnesium carbonate and/or the like. These compositions take the form of solutions, suspensions, tablets, pills, capsules, sustained release formulations and/or powders. In certain defined embodiments, oral pharmaceutical compositions will comprise an inert diluent and/or assimilable edible carrier, and/or they may be enclosed in hard and/or soft shell gelatin capsule, and/or they may be compressed into tablets, and/or they may be incorporated directly with the food of the diet. For oral therapeutic administration, the active compounds may be incorporated with excipients and/or used in the form of ingestible tablets, buccal tables, troches, capsules, elixirs, suspensions, syrups, wafers, and/or the like. Such compositions and/or preparations should contain at least 0.1% of active compound. The percentage of the compositions and/or preparations may, of course, be varied and/or may conveniently be between about 2 to about 75% of the weight of the unit, and/or preferably between 25–60%. The amount of active compounds in such therapeutically useful compositions is such that a suitable dosage will be obtained.

The tablets, troches, pills, capsules and/or the like may also contain the following: a binder, as gum tragacanth, acacia, cornstarch, and/or gelatin; excipients, such as dicalcium phosphate; a disintegrating agent, such as corn starch, potato starch, alginic acid and/or the like; a lubricant, such as magnesium stearate; and/or a sweetening agent, such as sucrose, lactose and/or saccharin may be added and/or a flavoring agent, such as peppermint, oil of wintergreen, and/or cherry flavoring. When the dosage unit form is a capsule, it may contain, in addition to materials of the above type, a liquid carrier. Various other materials may be present as coatings and/or to otherwise modify the physical form of the dosage unit. For instance, tablets, pills, and/or capsules may be coated with shellac, sugar and/or both. A syrup of elixir may contain the active compounds sucrose as a sweetening agent methyl and/or propylparabens as preservatives, a dye and/or flavoring, such as cherry and/or orange flavor.

The examples of pharmaceutical preparations described above are merely illustrative and not exhaustive; the nanoparticles of the present invention are amenable to most common pharmaceutical preparations.

Lipids and Liposome Delivery Methods

Other delivery methods of the present invention comprise a novel composition comprising one or more lipids associated with at least one nanoshell. A lipid is a substance that is characteristically insoluble in water and extractable with an organic solvent. Lipids include, for example, the substances comprising the fatty droplets that naturally occur in the cytoplasm as well as the class of compounds which are well known to those of skill in the art which contain long-chain aliphatic hydrocarbons and their derivatives, such as fatty acids, alcohols, amines, amino alcohols, and aldehydes. Of course, compounds other than those specifically described herein that are understood by one of skill in the art as lipids are also encompassed by the compositions and methods of the present invention. This invention also encompasses other host-guest complexation schemes such as those wherein the host molecules may be crown ethers, cyclodextrins, micelles, among others.

A lipid may be naturally occurring or synthetic (i.e., designed or produced by man). However, a lipid is usually a biological substance. Biological lipids are well known in the art, and include for example, neutral fats, phospholipids, phosphoglycerides, steroids, terpenes, lysolipids, glycosphingolipids, glycolipids, sulphatides, lipids with ether and ester-linked fatty acids and polymerizable lipids, and combinations thereof In particular embodiments, a lipid comprises a liposome. A liposome is a generic term encompassing a variety of single and multilamellar lipid vehicles formed by the generation of enclosed lipid bilayers or aggregates. Liposomes may be characterized as having vesicular structures with a bilayer membrane, generally comprising a phospholipid, and an inner medium that generally comprises an aqueous composition.

A multilamellar liposome has multiple lipid layers separated by aqueous medium. They form spontaneously when lipids comprising phospholipids are suspended in an excess of aqueous solution. The lipid components undergo self-rearrangement before the formation of closed structures and entrap water and dissolved solutes between the lipid bilayers (Ghosh and Bachhawat, 1991). Lipophilic molecules or molecules with lipophilic regions may also dissolve in or associate with the lipid bilayer.

In particular embodiments, a lipid and/or nanoshell may be, for example, encapsulated in the aqueous interior of a liposome, interspersed within the lipid bilayer of a liposome, attached to a liposome via a linking molecule that is associated with both the liposome and the nanoshell, entrapped in a liposome, complexed with a liposome, etc.

A liposome used according to the present invention can be made by different methods, as would be known to one of ordinary skill in the art. Phospholipids can form a variety of structures other than liposomes when dispersed in water, depending on the molar ratio of lipid to water. At low ratios the liposome is the preferred structure.

Liposomes can be prepared in accordance with other known laboratory procedures (e.g., see Bangham et al., 1965; Gregoriadis, 1979; Deamer and Uster 1983, Szoka and Papahadjopoulos, 1978, each incorporated herein by reference in relevant part). These methods differ in their respective abilities to entrap aqueous material and their respective aqueous space-to-lipid ratios.

The size of a liposome varies depending on the method of synthesis. Liposomes in the present invention can be a variety of sizes. In certain embodiments, the liposomes are small, e.g., less than about 100 nm, about 90 nm, about 80 nm, about 70 nm, about 60 nm, or less than about 50 nm in external diameter. In preparing such liposomes, any protocol described herein, or as would be known to one of ordinary skill in the art may be used. Additional non-limiting examples of preparing liposomes are described in U.S. Pat. Nos. 4,728,578, 4,728,575, 4,737,323, 4,533,254, 4,162,282, 4,310,505, and 4,921,706; International Applications PCT/US85/01161 and PCT/US89/05040; U.K. Patent Application GB 2193095 A; Mayer et al., 1986; Hope et al., 1985; Mayhew et al. 1987; Mayhew et al., 1984; Cheng et al., 1987; and Liposome Technology, 1984, each incorporated herein by reference).

Liposomes interact with cells to deliver agents via four different mechanisms: Endocytosis by phagocytic cells of the reticuloendothelial system such as macrophages and/or neutrophils; adsorption to the cell surface, either by non-specific weak hydrophobic and/or electrostatic forces, and/or by specific interactions with cell-surface components; fusion with the plasma cell membrane by insertion of the lipid bilayer of the liposome into the plasma membrane, with simultaneous release of liposomal contents into the cytoplasm; and/or by transfer of liposomal lipids to cellular and/or subcellular membranes, and/or vice versa, without any association of the liposome contents. Varying the liposome formulation can alter which mechanism is operative, although more than one may operate at the same time.

Targeted delivery is achieved by the addition of ligands without compromising the ability of these liposomes deliver large amounts of nanoshells. It is contemplated that this will enable delivery to specific cells, tissues and organs. The targeting specificity of the ligand-based delivery systems are based on the distribution of the ligand receptors on different cell types. The targeting ligand may either be non-covalently or covalently associated with the lipid complex, and can be conjugated to the liposomes by a variety of methods.

The targeting ligand can be either anchored in the hydrophobic portion of the complex or attached to reactive terminal groups of the hydrophilic portion of the complex. The targeting ligand can be attached to the liposome via a linkage to a reactive group, e.g., on the distal end of the hydrophilic polymer. Preferred reactive groups include amino groups, carboxylic groups, hydrazide groups, and thiol groups. The coupling of the targeting ligand to the hydrophilic polymer can be performed by standard methods of organic chemistry that are known to those skilled in the art. In certain embodiments, the total concentration of the targeting ligand can be from about 0.01 to about 10% mol.

Targeting ligands are any ligand specific for a characteristic component of the targeted region. Preferred targeting ligands include proteins such as polyclonal or monoclonal antibodies, antibody fragments, or chimeric antibodies, enzymes, or hormones, or sugars such as mono-, oligo- and poly-saccharides (see, Heath et al 1986) For example, disialoganglioside GD2 is a tumor antigen that has been identified neuroectodermal origin tumors, such as neuroblastoma, melanoma, small-cell lung carcenoma, glioma and certain sarcomas (Mujoo et al., 1986, Schulz et al., 1984). Liposomes containing anti-disialoganglioside GD2 monoclonal antibodies have been used to aid the targeting of the liposomes to cells expressing the tumor antigen (Montaldo et al., 1999; Pagan et al., 1999). In another non-limiting example, breast and gynecological cancer antigen specific antibodies are described in U.S. Pat. No. 5,939,277, incorporated herein by reference. In a further non-limiting example, prostate cancer specific antibodies are disclosed in U.S. Pat.

No. 6,107,090, incorporated herein by reference. Thus, it is contemplated that the antibodies described herein or as would be known to one of ordinary skill in the art may be used to target specific tissues and cell types in combination with the compositions and methods of the present invention. In certain embodiments of the invention, contemplated targeting ligands interact with integrins, proteoglycans, glycoproteins, receptors or transporters. Suitable ligands include any that are specific for cells of the target organ, or for structures of the target organ exposed to the circulation as a result of local pathology, such as tumors.

In certain embodiments of the present invention, in order to enhance the transduction of cells, to increase transduction of target cells, or to limit transduction of undesired cells, antibody or cyclic peptide targeting moieties (ligands) are associated with the lipid complex. Such methods are known in the art. For example, liposomes have been described further that specifically target cells of the mammalian central nervous system (U.S. Pat. No. 5,786,214, incorporated herein by reference). The liposomes are composed essentially of N-glutarylphosphatidylethanolamine, cholesterol and oleic acid, wherein a monoclonal antibody specific for neuroglia is conjugated to the liposomes. It is contemplated that a monoclonal antibody or antibody fragment may be used to target delivery to specific cells, tissues, or organs in the animal, such as for example, brain, heart, lung, liver, etc.

Still further, a nanoshell may be delivered to a target cell via receptor-mediated delivery and/or targeting vehicles comprising a lipid or liposome. These take advantage of the selective uptake of macromolecules by receptor-mediated endocytosis that will be occurring in a target cell. In view of the cell type-specific distribution of various receptors, this delivery method adds another degree of specificity to the present invention.

Thus, in certain aspects of the present invention, a ligand will be chosen to correspond to a receptor specifically expressed on the target cell population. A cell-specific nanoshell delivery and/or targeting vehicle may comprise a specific binding ligand in combination with a liposome. The nanoshell to be delivered are housed within a liposome and the specific binding ligand is functionally incorporated into a liposome membrane. The liposome will thus specifically bind to the receptor(s) of a target cell and deliver the contents to a cell. Such systems have been shown to be functional using systems in which, for example, epidermal growth factor (EGF) is used in the receptor-mediated delivery of a nucleic acid to cells that exhibit upregulation of the EGF receptor.

In still further embodiments, the specific binding ligand may comprise one or more lipids or glycoproteins that direct cell-specific binding. For example, lactosyl-ceramide, a galactose-terminal asialganglioside, have been incorporated into liposomes and observed an increase in the uptake of the insulin gene by hepatocytes (Nicolau et al., 1987). The asialoglycoprotein, asialofetuin, which contains terminal galactosyl residues, also has been demonstrated to target liposomes to the liver (Spanjer and Scherphof, 1983; Hara et al., 1996). The sugars mannosyl, fucosyl or N-acetyl glucosamine, when coupled to the backbone of a polypeptide, bind the high affinity manose receptor (U.S. Pat. No. 5,432,260, specifically incorporated herein by reference in its entirety). It is contemplated that the cell or tissue-specific transforming constructs of the present invention can be specifically delivered into a target cell or tissue in a similar manner.

In another example, lactosyl ceramide, and peptides that target the LDL receptor related proteins, such as apolipoprotein E3 ("Apo E") have been useful in targeting liposomes to the liver (Spanjer and Scherphof, 1983; WO 98/0748).

Folate and the folate receptor have also been described as useful for cellular targeting (U.S. Pat. No. 5,871,727). In this example, the vitamin folate is coupled to the complex. The folate receptor has high affinity for its ligand and is over-expressed on the surface of several malignant cell lines, including lung, breast and brain tumors. Anti-folate such as methotrexate may also be used as targeting ligands. Transferrin mediated delivery systems target a wide range of replicating cells that express the transferrin receptor (Gilliland et al., 1980).

Binding of Conjugated Nanoparticles to Cultured Cells

Nanoparticles (absorber/scatterers and emitters) can be linked to cell-specific antibodies or peptides in order to cause targeted binding of an injectable nanoparticle formulation to a specific tissue or cell type, particularly cancerous prostate epithelial cells. Nanoshells and nanoemitters can be prepared with surface-bound, cell-specific antibodies, such as antibodies directed against prostate specific membrane antigen. Cultured cells that are either targeted for nanoparticle conjugate binding or that serve as non-specific controls are exposed to nanoparticle suspensions then rinsed thoroughly to remove unbound particles. Nanoparticle binding to cell surfaces can be assessed via environmental scanning electron microscopy (ESEM).

In vitro and In vivo Procedures

A skilled artisan realizes that the nanoshells of the present invention can be employed in a variety of types of experimental procedures, for example, but not limited to in vitro or in vivo experimental procedures.

Briefly, in vitro assays are quick, inexpensive and easy assays to run. Such assays generally use isolated molecules, such as cells, and can be run quickly and in large numbers, thereby increasing the amount of information obtainable in a short period of time. A variety of vessels may be used to run the assays, including test tubes, plates, dishes and other surfaces.

Various cell lines can be utilized for these assays, including cells specifically engineered for this purpose. Numerous cell lines and cultures are available for use, and they can be obtained through the American Type Culture Collection (ATCC), which is an organization that serves as an archive for living cultures and genetic materials (www.atcc.org). In certain embodiments, a cell may comprise, but is not limited to, at least one skin, bone, neuron, axon, cartilage, blood vessel, cornea, muscle, facia, brain, prostate, breast, endometrium, lung, pancreas, small intestine, blood, liver, testes, ovaries, cervix, colon, skin, stomach, esophagus, spleen, lymph node, bone marrow, kidney, peripheral blood, embryonic or ascite cell, and all cancers thereof.

Depending on the assay, culture of the cells may be required. The cell is examined using any of a number of different physiologic assays. Such parameters include measurements of apoptosis, toxicity and cell death. These measurements are preformed using standard technqiues well known and used in the art. Alternatively, molecular analysis may be performed, for example, looking at protein expression, mRNA expression (including differential display of whole cell or polyA RNA) and others.

In further embodiments, a tissue may comprise a cell or cells to be transformed with a nanoshell of the present invention. The tissue may be part or separated from an organism. In certain embodiments, a tissue may comprise, but is not limited to, adipocytes, alveolar, ameloblasts, axon, basal cells, blood (e.g., lymphocytes), blood vessel, bone, bone marrow, brain, breast, cartilage, cervix, colon, cornea, embryonic, endometrium, endothelial, epithelial, esophagus, facia, fibroblast, follicular, ganglion cells, glial cells, goblet cells, kidney, liver, lung, lymph node, muscle, neuron, ovaries, pancreas, peripheral blood, prostate, skin, skin, small intestine, spleen, stem cells, stomach, testes, ascite tissue, and all cancers thereof.

Additional in vivo assays involve the use of various animal models, including transgenic animals that have been engineered to have specific defects, or carry markers that can be used to measure the ability of a nanoshell of the present invention to effect different cells or tissues within the organism. Due to their size, ease of handling, and information on their physiology and genetic make-up, mice are a preferred embodiment, especially for transgenics. However, other animals are suitable as well, including rats, rabbits, hamsters, guinea pigs, gerbils, woodchucks, cats, dogs, sheep, goats, pigs, cows, horses and monkeys (including chimps, gibbons and baboons).

In such assays, one or more compositions of nanoshells of the present invention are administered to an animal, and the ability of the nanoshells to alter cell proliferation, cell toxicity and/or apoptosis is compared to a similar animal not treated with the nanoshell.

Treatment of these animals with nanoshells will involve the administration of the nanoshells, in an appropriate form, to the animal. Administration will be by any route that could be utilized for clinical or non-clinical purposes, including but not limited to intradermal, subcutaneous, intramuscular, intraperitoneal or intravenous injection. Specifically contemplated routes are systemic intravenous injection, regional administration via blood or lymph supply, or directly to an affected site.

tions. Therefore photoinduced local heating of nanoshells which are conjugated to antibodies which target cells (such as tumor or non-tumor cells) should lead to local, specific cell death. This type of inhibition can be useful in a variety of clinical conditions, for example but not limited to, tumors (malignant or benign) inflammatory responses or autoimmune diseases.

More generally, the nanoshell of the present invention may be used in an amount effective to kill or inhibit proliferation of a cancer cell. This process may involve contacting the cell(s), tissue or organism with the nanoshell of the present invention to produce a desired therapeutic benefit. This may be achieved by contacting the cell, tissue or organism with a single composition or pharmacological formulation that includes the nanoshell and one or more agents, or by contacting the cell with two or more distinct compositions or formulations, wherein one composition includes a nanoshell and the other includes one or more agents.

The terms contacted and exposed, when applied to a cell, tissue or organism, are used herein to describe the process by which a therapeutic nanoshell of the present invention and/or another agent, such as for example a chemotherapeutic or radiotherapeutic agent, are delivered to a target cell, tissue or organism or are placed in direct juxtaposition with the target cell, tissue or organism. To achieve cell killing or stasis, the nanoshell and/or additional agent(s) are delivered to one or more cells in an effective amount to kill the cell(s) or prevent them from dividing.

Various combination regimens of the nanoshells and one or more agents may be employed. Non-limiting examples of such combinations are shown below, wherein a composition nanoshells is "A" and an agent is "B":

| A/B/A | B/A/B | B/B/A | A/A/B | A/B/B | B/A/A | A/B/B/B | B/A/B/B |
|-------|-------|-------|-------|-------|-------|---------|---------|
| B/B/B/A | B/B/A/B | A/A/B/B | A/B/A/B | A/B/B/A | B/B/A/A | | |
| B/A/B/A | B/A/A/B | A/A/A/B | B/A/A/A | A/B/A/A | A/A/B/A | | |

Therapeutic Methods

Unlike molecular fluorophores, metal nanoshells are not generally subject to photobleaching or photoinduced damage. Since the nanoshell resonance decays nonradiatively (with typical quantum efficiencies of a few percent), most of the energy due to optical absorption is converted into heat. Thus resonant illumination of highly absorptive metal nanoshells can provide significant local heating to the microscopic environment of the nanoshells. In illustration of this effect can be used to provide significant heat transfer to induce a phase transition in poly-N-isopropylacrylamide (NIPAAm), a polymer which undergoes an abrupt deswelling transition when raised above its lower critical solution temperature (LCST), nominally 45° C. (Sershen et al., 1999). When the copolymer is doped either homogeneously or heterogeneously with absorptive gold nanoshells, the deswelling transition is induced by irradiation with light at the nanoshell resonance wavelength (FIGS. 6a and 6b). This observation was verified against a control sample of copolymer without nanoshells, to confirm that the weak residual absorption of the copolymer at the irradiation wavelength was insufficient to induce a temperature rise and the resultant deswelling transition. This local heating effect can be observed at relatively modest power levels using either continuous or pulsed laser sources, at power levels significantly less intense than those used in bioimaging applica- Administration of the composition nanoshell to a cell, tissue or organism may follow general protocols for the administration of chemotherapeutics, taking into account the toxicity, if any. It is expected that the treatment cycles would be repeated as necessary. In particular embodiments, it is contemplated that various additional agents may be applied in any combination with the present invention.

Chemotherapeutic agents that may be used in combination with the present invention include, but are not limited to, 5-fluorouracil, bleomycin, busulfan, camptothecin, carboplatin, chlorambucil, cisplatin (CDDP), cyclophosphamide, dactinomycin, daunorubicin, doxorubicin, estrogen receptor binding agents, etoposide (VP16), farnesyl-protein transferase inhibitors, gemcitabine, ifosfamide, mechlorethamine, melphalan, mitomycin, navelbine, nitrosurea, plicomycin, procarbazine, raloxifene, tamoxifen, taxol, temazolomide (an aqueous form of DTIC), transplatinum, vinblastine and methotrexate, vincristine, or any analog or derivative variant of the foregoing. These agents or drugs are categorized by their mode of activity within a cell, for example, whether and at what stage they affect the cell cycle. Alternatively, an agent may be characterized based on its ability to directly cross-link DNA, to intercalate into DNA, or to induce chromosomal and mitotic aberrations by affecting nucleic acid synthesis. Most chemotherapeutic agents fall into the following categories:

alkylating agents, antimetabolites, antitumor antibiotics, corticosteroid hormones, mitotic inhibitors, and nitrosoureas, hormone agents, miscellaneous agents, and any analog or derivative variant thereof.

Chemotherapeutic agents and methods of administration, dosages, etc. are well known to those of skill in the art (see for example, the "Physicians Desk Reference", Goodman & Gilman's "The Pharmacological Basis of Therapeutics", "Remington's Pharmaceutical Sciences", and "The Merck Index, Eleventh Edition", incorporated herein by reference in relevant parts), and may be combined with the invention in light of the disclosures herein. Some variation in dosage will necessarily occur depending on the condition of the subject being treated. The person responsible for administration will, in any event, determine the appropriate dose for the individual subject. Examples of specific chemotherapeutic agents and dose regimes are also described herein. Of course, all of these dosages and agents described herein are exemplary rather than limiting, and other doses or agents may be used by a skilled artisan for a specific patient or application. Any dosage in-between these points, or range derivable therein is also expected to be of use in the invention.

The general method described herein is also useful where the targeted denaturation of proteins is desired. In such an application, the nanoshells are directed to the proteins of interest by any of the targeting methods discussed. Local induction of hyperthermia will then effect denaturation. The denaturation primarily proceeds by the break-up of hydrogen bonds and other noncovalent interactions, although other harsher denaturation processes are possible depending upon the extent of heating. The denaturation may be effected either in vivo or in vitro.

Another therapeutic application, amenable to all the aforementioned schemes, is a highly localized, rapid induction of hyperthermia. The heat cycle could be commenced with a burst of exciting radiation, causing intense highly localized heating and very little heating to the surrounding bulk tissue. In this way, collateral damage is minimized. Such an approach could be used to remove non-cellular non-tissue material, such as coronary plaque. The general methodology has additional uses in the area of cosmetic enhancements. Intense localized hyperthermia can be used kill fat cells or to remove unsightly skin formations, among other potential cosmetic applications.

Nanoshells can be used as a secondary therapy to deliver heat and enable other, primary therapies. For instance, the level of heating in and of itself may be insufficient to cause cell death. However, the elevated temperatures may facilitate or accentuate other therapies such as chemotherapy or gene therapy.

Diagnostic Methods

A variety of techniques for biomedical imaging with infrared diffusing light have been explored (Hebden, 1997). Time-gated methods, which involve the rejection of all photons except those traversing the sample via ballistic or quasi-ballistic trajectories, are conceptually straightforward; however, they favor the imaging of samples just a few millimeters in thickness. For biological samples of several centimeters in thickness, frequency domain approaches involving the detection of modulated laser light following its transmission through the tissue are particularly amenable. The resulting diffuse photon density waves (DPDW) are detected using demodulation schemes and analyzed and reconstructed using a range of methods (Jiang, et al, 1995; Li, et al, 1997; O'Leary, et al, 1995; Tromberg, et al., 1997). Sample-detector geometries for this type of imaging typically involve multiple source-detector arrays that maintain a constant source-detector distance around a cross section of the sample. Geometrics consisting of a single fixed light source and a scanned detector, which simplify data acquisition and reduce overall cost, are an extremely attractive simplification of this approach (Yang, et al, 1997).

Nanoshell-based Imaging

The sensitivity of current infrared diffuse photon imaging methods is based on the contrast differences between the absorption and scattering coefficients of malignant and normal tissue. Typical differences in absorption and scattering coefficients vary from 33% to 66% and from 6% to 30%, respectively, from patient to patient (Tromberg, supra, 1997). These small differences determine image contrast, and therefore image resolution—typically just under 1 cm, again varying from patient to patient. There is therefore great interest in the use of specific contrast agents that would selectively target one type of tissue and enhance the contrast, and therefore the resolution, of the tomographic image. While this is a customary approach in biomedical imaging methods such as MRI and PET, there are very few contrast agents suitable for near infrared imaging. Only the tricarboxycyanine dyes, of which the best known member is indocyanine green (cardiogreen) have been approved for human use (Chance, 1993).

In contrast to indocyanine green, gold nanoshells have a million-fold enhancement in optical extinction: $10^{-15}$–$10^{-16}$ $cm^2$ per molecule compared with $10^{-9}$–$10^{-10}$ $cm^2$ per nanoparticle (100 nm diameter). In addition, for indocyanine dyes, the optical extinction is almost purely absorptive, whereas gold nanoshells can be fabricated either as scatterers or absorbers, to enhance either coefficient appropriately, as required.

Nanoemitter-based Imaging

There has been considerable interest in the use of fluorescent dyes as contrast agents to differentiate diseased from normal tissue. Although dyes that excite and emit in the near infrared have been developed, which in principle would facilitate fluorescent imaging of diseased tissue deep in the body, issues such as low uptake and rapid photobleaching present significant problems regarding their utility. However, considerable interest remains, since the potential for correlating fluorescence lifetimes with tissue properties may provide important local information in the resulting fluorescence-based image (Paithankar, et al, 1997). Virtually all interest in this field has focused on molecular fluorophores, primarily due to their fast fluorescence lifetimes (typically 1–100 nanoseconds) which permit modulation techniques similar to those used in non-fluorescent infrared tomography.

Rare earth doped nanoemitters have several properties that contrast with molecular fluorophores. Due to the encapsulation of the emissive ions in the silica nanoparticle matrix, the local environment in which the nanoparticle resides does not influence the nanoemitter fluorescence properties, as is the case for free molecular fluorophores. The concentration of rare earth emitters within silica nanoparticles (typically a few percent) can be increased until the concentration is sufficient for self-quenching of the fluorescence to occur. Because of the high dopant density, the nanoemitters will exhibit much greater absorption than would be typical for isolated rare earth ionic species, as much brighter fluorescence.

In contrast to molecular fluorophores, rare earth ions have extremely long fluorescent lifetimes, often hundreds of microseconds in duration. This property eliminates the possibility of modulating the fluorescence of the nanoparticles by modulating the input beam of the excitation laser. However, the recent demonstration of ultrasonic modulation of scattered light in turbid media presents a useful method for modulating the nanoemitter fluorescence (L. V. Wang, 1998). With the addition of ultrasonic modulation, the frequency modulated detection strategy used in the nanoshell experiments can be used in fluorescence imaging with rare earth nanoemitters.

Imaging based on the fluorescence of targeted nanoemitters should provide an increase in resolution relative to conventional infrared tomographic imaging methods. This is because the actual light source, that is, the nanoemitters themselves, will reside in or on the heterogeneity to be imaged. Since object resolution in turbid media scales linearly with the optical path length, the optical path length from scattered light originating within the sample is naturally shorter than the optical path length in a conventional transmissive imaging geometry. This could result in an average increase of resolution of a factor of two over transmissive imaging. Further increases in resolution will be obtainable due to the changes in $\mu_a$ and $\mu_s$ due to the presence of the nanoemitters themselves.

To eliminate shadowing effects, fluorescence imaging requires the excitation of the sample from a variety of directions, and multi-source, multidetector geometry. This type of experimental geometry lends itself to emission/transmission imaging, where reconstructed image quality can be improved by performing both emissive imaging as well as standard transmission imaging on the sample of interest, a strategy commonly applied to positron emission tomography (PET) (Tung, et al, 1992).

Therapeutic Methods Using Gold Nanoshells

Figure 7:
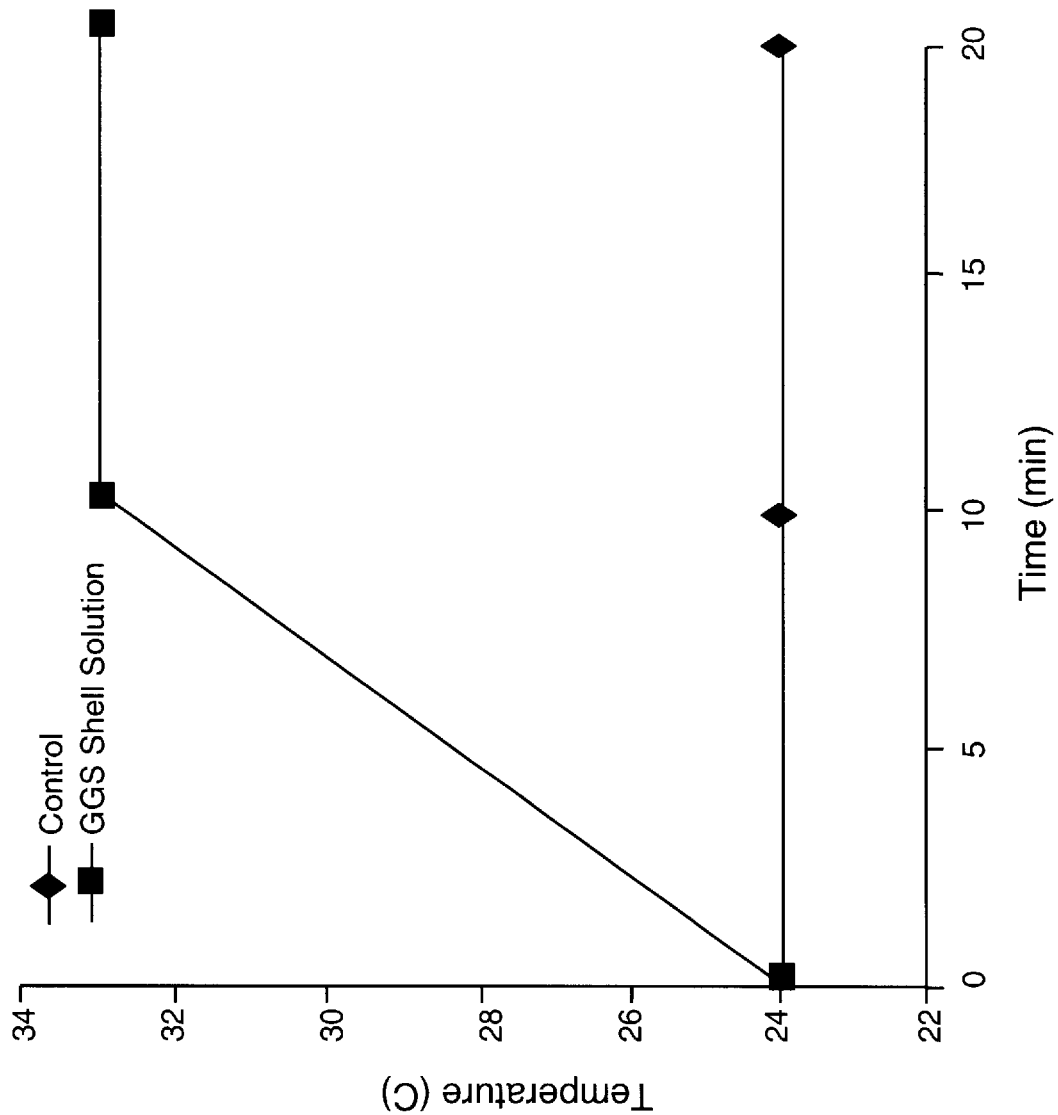
FIG. 7 is a graph of temperature rise due to irradiation at 850 nm at a power level of 500 mW of a gold nanoshell solution resonant at 850 nm (squares); aqueous control (diamonds).

Under modest laser irradiation, gold nanoshells can induce a significant temperature rise in their local environment. In a polyNIPAAm matrix, the local heating is sufficient to initiate a deswelling transition, corresponding to a temperature increase of approximately 8 degrees. This temperature increase has been measured directly in a solution of gold nanoshells in water, and is shown in FIG. 7. In this experiment, a picomolar solution of gold nanoshells with a resonance at 850 nm was irradiated on resonance with a 500 mW continuous wave Ti:Sapphire laser for a total of 20 minutes. After the first ten minutes of irradiation, a 9 degree temperature increase was observed. Heat loss to the surroundings prevented further heating of the sample upon continued irradiation. An aqueous control solution irradiated in the same manner showed no detectable temperature rise.

This local selective heating in the vicinity of gold nanoshells can be applied for the thermal destruction of cancerous cells. Experiments were performed which demonstrate that gold silica nanoshells can be used to specifically target carcinoma cells using the anti c-erB-2 (or HER2) antibody. This antibody targets the overexpressed HER2 tyrosine kinase receptor commonly found on the surfaces of many human breast epithelial carcinomas. After binding Near-IR absorbing nanoshells to these carcinoma cells using this antibody, we irradiate the samples with Near IR light, heating the nanoshells and destroying the neighboring carcinomas.

The following examples are included to demonstrate preferred embodiments of the invention. The examples are merely illustrative and not exhaustive of the applications of the present invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

General Method for Metal Nanoshell Colloid Based Synthesis

Versatile methods for the synthesis of nanoparticle cores and metal shells of defined sizes have been developed and are described below. Generally, the method comprised the following steps:

1. A dielectric or semiconductor nanoparticle core was obtained and dispersed in solution;
2. 1–2 nm metal-like "seed" colloids were attached to the surface of the nanoparticle core via molecular linkages, covering the core surface with a discontinuous metal colloid layer;
3. Additional metal was deposited onto the metal-like adsorbates by a solution phase chemical reduction reaction.

This nanoparticle assembly method was carried out with silica nanoparticles and gold colloid. Both commercially available silica nanoparticles and silica nanoparticles grown in situ were used successfully. The organosilane linkage molecule 4-aminopropyltriethoxy silane was absorbed onto the nanoparticle core. Gold colloid was then introduced into a solution containing the core particles. The gold colloidal nanoparticles bound to the organosilane linker molecules and covered the silica cores with a discontinuous layer of metal clusters. Subsequently, gold metal atoms were deposited onto the tethered metal clusters by reduction from solution.

EXAMPLE 2

Core Particle Synthesis

Initially a core material for the nanoparticle was prepared. This material had a spherical shape, and was approximately uniform in size. The silica particles produced in the following procedure had a standard deviation of less than 10% (4% is routinely achievable).

The method of Stober, et al., 1968, incorporated herein by reference to the extent it provides such methods, was used to produce monodisperse silicon dioxide particle cores. Other methods are applicable. Tetraethyl orthosilicate (TEOS) 99.999% was obtained from Aldrich Chemical Co., sodium hydroxide was from Fluka Chemical Co. and highly purified water was obtained from a Millipore "TOTALQ" system that included "MILLIQ$^{UV}$" and "MILLIQ$^{RO}$" filters. All glassware was cleaned with chromic acid solution and thoroughly rinsed with "TOTALQ" water.

Variations in water, base concentration, and TEOS concentration were used to produce monodisperse silica spheres of various sizes. Temperature and electrolyte concentration also affected the final diameter of the particles. Generally, the following concentration ranges were used: 0.1 to 0.5 M TEOS, 0.5 to 17 M $H_2O$, and 0.5 to 3.0 M ammonia. In addition, a variety of alcohols were used as solvents, however, ethanol was preferred. Higher ammonia concentrations provide larger particles.

Uniform particles having a diameter of 120 nm as measured by a transmission electron microscope (TEM) were prepared by the following method. Approximately 50 milliliters (ml) of dry (100%) ethanol and 4 ml of $NH_4OH$ (25% $NH_3$ in water), were stirred in a glass beaker. To this solution, 2.2 ml of tetraethyl orthosilicate having a purity of at least 99.999% was added and allowed to stir for at least 8 hours. By varying the concentrations of $NH_4OH$, water and silicate among other factors, the size of the silica particle was varied from approximately 20 nm to 500 nm diameter. Larger core particles were grown using a seeded growth technique where additional TEOS and water were added to already formed silica particles. Multiple additions of small amounts of additional reactants allowed monodisperse core particles to be grown as large as 4 microns.

EXAMPLE 3
Linker Molecule Attachment

To assemble a metallic shell around an inner layer frequently required the use of linker molecules. These molecules were chemically linked to the inner layer and served to bind atoms, ions, atomic or molecular clusters of the conducting shell to the inner layer. The conducting shell atoms that bound to the linkers were used as nucleation sites for reduction of the additional atoms or molecules to complete the shell. One method used to attach gold particles to silicon dioxide was to treat the particles with aminopropyltriethoxy silane (APTES). The silanol end groups of the APTES molecules attach covalently to the silica core extending their amine groups outward as a new termination of the particle surface.

In this method, 10 ml of a silica particle suspension such as prepared in Example III, was added to a 50 ml glass beaker. Next, pure aminopropyltriethoxy silane (APTES) was added to the solution. Based on estimates, enough silane was added to coat the particles with multiple layers of silane. For example, 40 $\mu L$ of undiluted APTES was used for particles having diameters of 120 nm. The solution was stirred for 2 hours, diluted to 200 mls and then heated to a boil for four hours. The heating step promotes the reaction of silanol groups into Si—O—Si bonds and strengthens the attachment of the silane to the silica. This mixture was centrifuged at 2000×g for 30 minutes. The supernatant was decanted off and the pellet was redispersed ultrasonically. This washing procedure was repeated five times.

Many linker molecules other than aminopropyltriethoxysilane are suitable for use in this procedure. For example, aminopropyltrimethoxysilane, diaminopropyldiethoxysilane, or 4-aminobutyl dimethylmethoxysilane and the like can be used. In addition, the surface can be terminated with a linker that allows for the direct reduction of metal atoms on the surface rather than through a metallic cluster intermediary. In other embodiments, reaction of tetrahydrothiophene(AuCl) with a silica core coated with diphenyltriethoxysilane leaves a surface terminated with gold chloride ions which can provide sites for additional gold reduction. In other embodiments, a thin shell of another nonmetallic material, such as CdS or CdSe grown on the exterior of a silica particle allows for a metallic shell to be reduced directly onto the nanoparticle's surface. In other embodiments, functionalized oligomers of conducting polymers can be attached in solution to the functionalized or nonfunctionalized surface of the core nanoparticle and subsequently cross-linked by thermal or photo-induced chemical methods.

EXAMPLE 4
Attachment of Metal Clusters

Metal clusters were attached to the linker molecules on the core by immersing the derivatized core particles in a metal colloid bath. Any metal that can be made in colloidal form could be attached as a metal cluster. For example, silver, platinum, palladium, lead and the like could be used. In addition, metal-like organic molecules are suitable. Such compounds include polyacetylene and polyaniline. Gold clusters having a diameter of 1–3 nm were grown using the reduction reaction as described by Duff, incorporated herein by reference to the extent such methods are disclosed. A solution of 45 ml of water, 300 $\mu L$ of 1 M NaOH and 1 mL of a freshly diluted 1% aqueous solution of tetrakis (hydroxymethyl)phosphonium chloride (THPC) was stirred in a 100 ml flat bottom beaker with a pyrex coated magnetic stir bar. After 2 minutes, 2 ml of chloroauric acid (25 mM dark-aged stock solution, hydrogen tetrachloroaurate (III) trihydrate 99.999% from Aldrich) was added. This reaction mix was used to form gold particles in solution with an average particle diameter of 1–2 nm. To increase the size of the particles higher concentrations of gold chloride could be used. Particles prepared in this fashion were referred to as ultra small gold particles or (UG).

Generally, the UG solution was mixed with silica particles in an amount that would theoretically cover the core particle surface five to ten times. The solution was allowed to react for 3 hours under gentle stirring. In the preferred embodiment the gold was used 5–30 days after it was made.

Typically, after three hours, unreacted gold colloid was separated from the gold-decorated silica particles by centrifugation at 1000 RCF. The minimum amount of centrifugal force required to effect separation was used to avoid coalescence of the particles. Particles were washed twice by resuspension and centrifugation.

The inventors made the surprising discovery that the gold decorated particles did not aggregate after being centrifuged and redispersed in the absence of additional stabilizing compounds. This discovery allowed the convenient separation of the decorated silica from colloidal gold, leaving the gold attached to silica in a chemically reactive state. Various protectants could be added before centrifugation to facilitate later resuspension of the particles. These protectants include polyvinyl alcohol, polyethylene glycol or phosphine ligands, and thiol-terminated carboxylic acid linkages. Resuspension was easily accomplished when a minimum amount of force was used in the centrifugation step and any aggregates of particles could be redispersed by treatment with sonification. A dynamic light scattering instrument was used according to standard and well known methods to verify that the particles were dispersed. The dispersed particles were diluted to 10 mls and used as a stock solution for the growth of the complete metal shell.

EXAMPLE 5
Growth of the Shell

The metal clusters were enlarged by deposition of gold using a variety of reductants such as hydroxylamine hydrocholoride, sodium borohydride, and formaldehyde. Formaldehyde was preferred. A solution of 25 mg anhydrous potassium carbonate was added to 100 ml of water containing 1.5 ml of 25 mM chloroauric acid solution (PCG). This solution was allowed to age in the dark for one day. Approximately 10 ml+/−5 ml of PCG was rapidly stirred with 2–5 mls of the gold clustered silica solution. A 100 $\mu L$ aliquot of freshly prepared formaldehyde solution (2% by volume in water) was slowly added.

Before enlargement of the metal clusters, the metal clusters attached to the particles had the same UV-visible absorption spectrum as their natural colloidal form. As additional metal was deposited onto the clusters, the absorbance maximum of the particle shifted to longer wavelengths, as shown in the lower curves of FIG. 3. When the gold shell was complete, the particles' absorbance maximum was related to its geometry, specifically, to the ratio of the thickness of the inner nonconducting layer to the thickness of the outer conducting layer. As the conducting layer grew thicker, the absorbance maximum of the particle shifted to shorter wavelengths, as shown in the upper curves of FIG. 3. The progress of this reaction was followed spectrophotometrically and terminated when the desired wavelength for the absorbance maximum was obtained. Typically a color change occurred within 10 minutes. For 110 nm diameter core particles, typically a visible color change is apparent, from faint brown to purple, blue, green, or yellow. Some of the other factors that influenced the optical absorption of the spectrum are the size of the core, the roughness of the shell, the shape of the core, additional reactants in solution that may be incorporated into the core during the reduction, the continuity of the shell, and the degree of aggregation of the particles.

Many different methods can be used to complete the metal shell once the nucleation sites are in place. One of skill in the art will realize that any method that can be used to develop a metal colloid into a larger metal colloid should be successful for the shell growth. For example, silver solutions such as the commercially available LI silver from Nanoprobes, Inc. may work. In addition, it is not necessary that the tethered seed particle be of the same material as the shell material. In one embodiment silver nitrate is reduced onto silica coated with UG. This is done in a basic solution with formaldehyde as a reductant and results in a silver shell. Photo-induced deposition of the metal shell onto the prepared nanoparticle surface is also possible.

Direct reduction of silver onto a non-conducting core can be accomplished with the reduction of silver directly onto a CdS semiconductor layer. In order to construct a CdS with a diameter greater than 20 nm it was necessary to first grow a CdS layer onto a silica core. This can be accomplished using water in oil microemulsions, for example. In one embodiment silver was reduced onto a silica/CdS particle by adding the particles to a solution of $AgNO_3$ and $NH_4$ and then slowly adding a $NH_3OHCl$ solution to develop the shell.

EXAMPLE 6

Gold nonoshells with a 37 nm diameter gold sulfide core and a gold shell thickness of 4 nm were formed by combining 20 mL of 2 mM $HAuCl_4$ and 28 mL of 1 mM $Na_2S$. The progress of the reaction can be monitored using a UV-visible to observe the extinction spectrum of the solution from 400–1050 nm. As the nanoshells formed, the extinction spectra exhibits a peak that red-shifted into the IR, then halted and began to blue-shift into the visible spectrum. The peak narrows and increases in magnitude as this occurs. Mercaptoproprionic acid (3.5 $\mu L$) is added to halt this shift (by halting the growth of the gold shell) when the extinction peaked is centered around 1050 nm. The solution then is brought to pH 10.5 with 1 M NaOH, centrifuged at 3000 RPM for 20 min four times, and stored at 4° C. The size and polydispersity of the resulting nanoshells may be determined by evaporating a drop of the nanoshell solution onto a carbon film on a copper grid and viewing the nanoshells via transmission electron microscopy.

EXAMPLE 7

Nanoengineered Thermal Management Materials and Coatings

The present application takes advantage of the fact that the sun's maximum radiant power that reaches the Earth's surface is distributed broadly across the visible and infrared regions of the electromagnetic spectrum and a mixture of nanoparticles can be developed to either absorb or scatter energy throughout that entire spectrum. The present technology is the only method known for systematic control of absorption or scattering of radiation across the entire range of the solar emission spectrum. A mixture of these particles is capable of absorbing radiation across the entire solar spectrum.

Such a mixture can be incorporated into polymers, glasses, paints, epoxies, or other coating matrices by standard methods well known in the art. The thermal properties of these materials can then be used in appropriate applications that rely on absorption and scattering of solar energy or any source of electromagnetic radiation across the wavelength range of the mixture.

EXAMPLE 8

Phothermally Induced Cell Death of Human Breast Carcinoma Cells Using Gold Silica Nanoshells Step 1: Preparing the Antibody Solutions Two different antibodies are used in this experiment. The experimental treatment uses the Anti c-erB-2 antibody (Dako, A0485) which targets oncoproteins on the HTB-30 human breast epithelial carcinoma cell line. For a nonspecific control, we are using a donkey anti-sheep IgG antibody (Sigma, S2763), which should act as a nonspecific control and should not bind to the HTB-30 cell surfaces. Both antibody solutions were prepared in deionized water (pH 7.6) at a concentration of 100 $\mu g/ml$.

Step 2: Fabrication of Nanoshells and Conjugation with Antibodies

Nanoshells with a peak absorption at 820 nm were fabricated with a 64 nm core radius and a 14 nm thick gold shell at a concentration of $2.83 \times 10^9$ particles/ml using methods described previously (Oldenberg, 1998).

After rinsing the nanoshells in deionized water, they are ready for conjugation with the antibodies. It has been well documented that proteins, such as antibodies, readily adsorb onto gold nanoparticle surfaces under aqueous conditions (Horisberger, 1981); therefore, conjugating gold nanoshells with antibodies should be as simple as mixing the two ingredients.

Four test tubes were labeled 1–4; 2.7 ml of nanoshell stock solution was added to tubes 1–3, while 3.0 ml of Dulbecco's phosphate buffered saline (DPBS) was added to tube 4. 300 $\mu l$ of the Anti-c-erB-2 stock, Anti-sheep stock, and DI water were added to Tubes 1, 2, and 3 respectively. All tubes were mixed and incubated overnight at 2–4° C.

To block any additional protein adsorption sites on the nanoshell surface, bovine serum albumin (BSA) is added to a final concentration of 3% (wt) in tubes 1 and 2. Tube 3, or treatment 3, is not given BSA; this treatment will act as a positive control when incubated with the cells; its exposed gold surface should provide strong adsorption of nanoshells onto the surface proteins of the HTB-30 cells, resulting in a high density of nanoshells atop the cells.

Next, DPBS is added to Tubes 1–3 in order to make the solutions isotonic with the cell samples that they will be coming in contact with.

Step 3: Incubating the Nanoshells with the Cells

The HTB-30 carcinoma cells were grown to near confluence in 2, 12-well trays with McCoy's 5a cell growth medium containing 10% Fetal Bovine Serum (FBS). Tubes 1–4 were heated to 37° C., the cells were rinsed once with DPBS, and 0.5 ml of the contents in each tube was added to three wells in each tray. The nanoshells treatments were incubated over the cells for 1 hr at 37° C. on an orbital shaker.

Beyond this point, the experiment takes two separate paths in parallel. One of the trays will undergo silver enhancement staining; this technique grows additional silver on nanoshells attached to the cell surface in order to visualize the amount of nanoshell binding in each of the four treatments. The other tray will be treated with the near IR laser, followed by staining to determine phothermally induced cell death Laser Treatment Step 4: Rinsing Nanoshells from Cell Surface All well are rinsed three times with DPBS, then replaced with Serum Free McCoy's 5a medium.

Step 5: Irradiate Cells 2 of the 3 wells in each treatment (1–4) are irradiated with a Coherent™ diode laser emitting at 821 nm, at a dosage of 37 W/cm$^2$ for 10 minutes. When complete, the cells are incubated another 2 hrs at 37° C.

Step 6: Perform Viability Staining

The viability stain, Calcein AM, fluoresces green in live cells (converted to a fluorescent product be esterase activity in living cells). By comparing normal phase contrast images (which views all cells) and the Calcein AM stains (which detects only live cells), we may discern between live and dead cells within a sample.

The cells were rinsed once with DPBS and incubated with a 1 $\mu$M solution of Calcein AM for 45 min. at RT. The cells are then examined by fluorescence and phase contrast microscopy to assess cell viability.

Silver Staining

Step 4a: Rinse Nanoshells from Cell Surface and Fixation

Excess nanoshells are rinsed from the cell surface. The remaining nanoshells/cells are fixed in place using a 2.5% glutaraldehyde solution for 15 min. Samples are then rinsed in DI water to remove excess salts, which may interfere with the development of silver during the next step.

Step 5a: Silver Enhancement

A silver enhancement kit was purchased from Sigma (SE-100). Enhancement reagent A is mixed with reagent B in equal volumes and added to the samples. As the silver develops on the nanoshells, the samples become black. When sufficient development occurs (around 20 min), the samples are rinsed in DI water, followed by addition of 2.5% sodium thiosulfate, which stops the silver growth.

Step 6a: Counter Stain with Mayer's Hematoxylin

Hematoxylin stains the underlying cells blue, so that one can compare the location of the nanoshells and the underlying cells. A few drops is added atop the samples for 5 min. They are then rinsed with DI water, then treated with 37 mM ammonium hydroxide for 5 min. The cells are then mounted in Dako glycergel, covered with glass coverslips, and examined by phase contrast microscopy.

EXAMPLE 9

In vivo, Thermally-Induced Tissue Desctruction Using Laser Excited Nanoshells

Procedure

Skin was removed from the arm muscle of the triceps brachii of Wistar rats. In cases receiving nanoshell treatment, a gold/silica nanoshell suspension in physiological saline was injected intramuscularly (50 $\mu$L at $1\times10^{10}$/mL). Control samples received no injection. The muscle was then irradiated using a diode laser (832 nm emission), 3 mm spot diameter (16.7 W/cm$^2$). Control samples (no nanoshells) were irradiated for 7 minutes. Nanoshell treated samples were irradiated for 30 s.

Results

Figure 8A:
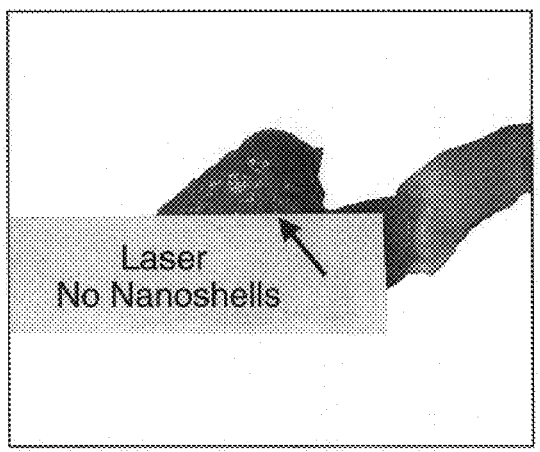
FIGS. 8a and 8b demonstrate in vivo results of tissue destruction experiments using nanoshells.
Figure 8B:
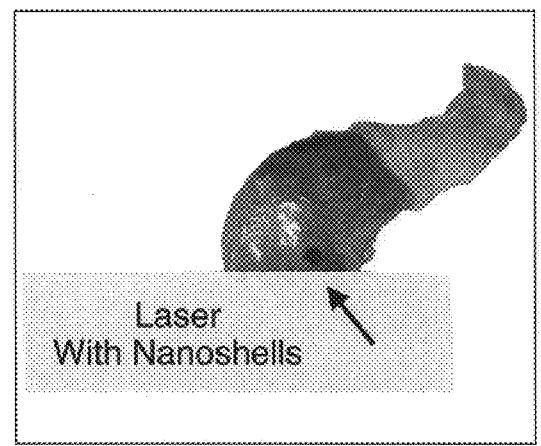
Figure 9A:
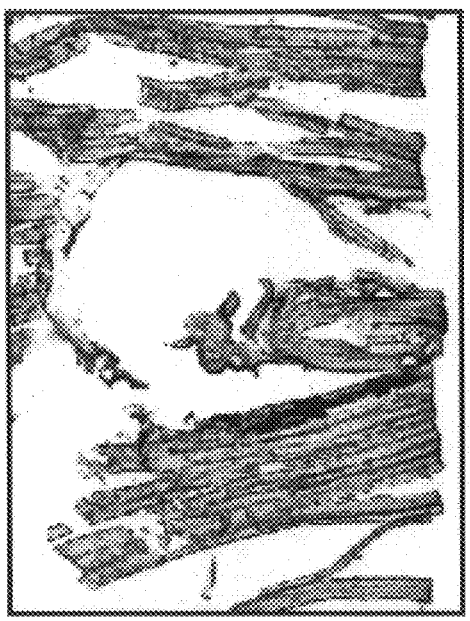
FIGS. 9a and 9b illustrate a histological section of tissue with thermal injury induced by exposure to near infrared light in the presence of nanoshells.
Figure 9B:
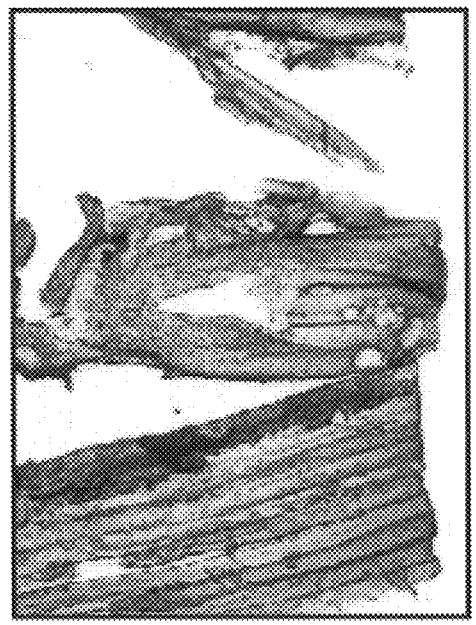

Exposure to the laser in the absence of nanoshells did not induce visible tissue damage. The tissues were injected with nanoshells before exposure to laser light, however, sustained extensive tissue damage. Tissue was carbonized within 30 s of irradiation at this power; irradiation was therefore terminated before the 7 min exposure target. FIG. 8a shows the control sample exposed to 7 min of laser irradiation. FIG. 8b shows the gross appearance of the tissue following exposure to the near infrared laser in the presence of nanoshells. The circular area of carbonized and coagulated tissue is easily visible in FIG. 8b.

REFERENCES CITED

All patents and publications mentioned in the specification are indicative of the level of those skilled in the art to which the invention pertains. All patents and publications are herein incorporated by reference to the same extent as if each individual publication was specifically and individually indicated to be incorporated by reference.

Ozzello, et al., *Breast Cancer Res. Treat.* 48(2):135–47 (1998).

Moro, et al., *Cancer Res.* 57(10):1922–8 (1997).

Sforzini, et al., *Br. J. Haematol.* 102(4):1061–8 (1998).

Zhu, et al., *J. Nucl. Med.* 39(1):65–76 (1998).

Gregorakis, et al., *Semin. Urol. Oncol.* 16(1):2–12 (1998).

Nedeljkovic et al. *Appl. Phys. Lett.,* 58:2461–63, (1991).

Yang, et al., *Hum. Gene Ther.* 9(13):1929–37 (1998).

Jiang, et al., *J. Virol.* 72(12):10148–56 (1998).

Chu & Dornburg, *J. Virol.* 71(1):720–5 (1997).

Somia, et al., *Proc. Natl. Acad. Sci. U.S.A.* 92(16):7570–4 (1995).

Pasqualini, et al., *Nat. Biotechnol.* 15(6):542–6 (1997).

Weissleder, *Nat. Biotechnol.* 17(4):375–8 (1999).

Averitt et al. *Phys. Rev. Lett.,* 78: 4217–20 (1997).

Weissleder, *Nat. Biotechnol.* 17(4):375–8 (1999).

Pathankar et al., *Applied Optics,* 36:2260–72, (1997).

Neeves & Birnboim, *J. Opt. Sci. Amer. B,* 6:787–92 (1989).

Kreibig and Vollmer, *Optical Properties of Metal Clusters,* New York, Springer, 1995.

Averitt et al., *J. Opt. Soc. Am. B,* 6:787–792, (1999).

Oldenburg et al., *Chem Phys. Lett.,* 288:243–47 (1998).

Sershen et al., *Proc. Soc. Biomat.,* 21:443, (1999).

Hebden, *Phys. Med. Biol.,* 42: 825–40, (1997).

Heath et al., *Chem. Phys. Lipids* 40:347 (1986).

Jiang, et al, *Optics Letters,* 20:2128–30, (1995).

Li, et al, *Optics Letters,* 22:573–75, (1997).

O'Leary, et al, *Optics Letters* 20:426–28, (1995).

Tromberg, et al, *Phys. Trans. R. Soc. Lond. B,* 352:661–68, (1997).

Yang, et al, *Optical Engineering,* 36:1562–69, (1997).

Chance, *Proc. Natl. Acad. Sci. U.S.A.* 90(8):3423–7 (1993).

Paithankar, et al, *Appl. Opt.,* 36:2260–72, (1997).

L. V. Wang, *Photchem. Photobiol.* 67:41–9, (1998).

Tung, et al, *IEEE Trans. Nucl. Sci.,* 39:1134–43, (1992).

Stober, et al. *J. Colloid. Interface Sci.,* 26: 62–9 ,(1968).

Horisberger, *Scan Elec. Microsc.,* 2:9–31, (1981).

Doolittle, et al, *Methods Mol Biol.,* 109:215–237, (1999).

Gulbis et al., *Hum Pathol* 24(12):1271–1285, (1993).

Nakamura et al, Enzyme Immunoassays: Heterogeneous and Homogeneous Systems, Chapter 27, 1987.

Ghosh et al. *Targeting of Liposomes to Hepatocytes,* In: Wu G. and C. Wu ed. *Liver Diseases, Targeted Diag-* nosis and Therapy Using Specific Receptors and Ligands, New York: Marcel Dekker, pp. 87–104, 1991.

Bangham, et al., *J. Mol. Biol.*, 13:238–252, (1965).

Gregoriadis (Ed.), *Drug Carriers in Biology and Medicine*, 287–341, 1979.

Deamer et al., In *Liposomes*, Ostro (Ed.), Marcel Dekker, Inc., New York, 27–52, 1983.

Szoka et al., *Proc. Natl. Acad. Sci.*, 75:4194–4198, (1978).

Mayer et al., *Annals Internal Medicine*, 104:194–96, (1986)

Mayhew *Methods Enzymol.* 149:64–77, (1987).

Cheng et al., *Invest Radiol.* 22(1):47–55, (1987).

*Antibodies: A Laboratory Manual,* Cold Spring Harbor Laboratories, Cold Spring Harbor, N.Y., 1988.

U.S. Pat. No. 5,023,139
U.S. Pat. No. 4,983,159
U.S. Pat. No. 4,106,488
U.S. Pat. No. 4,303,636
U.S. Pat. No. 4,728,578
U.S. Pat. No. 4,728,575
U.S. Pat. No. 4,737,323
U.S. Pat. No. 4,533,254
U.S. Pat. No. 4,162,282
U.S. Pat. No. 4,310,505
U.S. Pat. No. 4,921,706
U.S. Pat. No. 5,939,277
U.S. Pat. No. 6,107,090
U.S. Pat. No. 5,432,260
U.S. Pat. No. 5,871,727
U.S. Pat. No. 5,786,214
PCT/US85/01161
PCT/US89/05040
UK Patent Application GB 2193095
PCT WO 98/0748

One of skill in the art readily appreciates that the present invention is well adapted to carry out the objectives and obtain the ends and advantages mentioned as well as those inherent therein. Proteins, peptide fragments, splice variants, vectors, methods, procedures and techniques described herein are presently representative of the preferred embodiments and are intended to be exemplary and are not intended as limitations of the scope. Changes therein and other uses will occur to those skilled in the art which are encompassed within the spirit of the invention or defined by the scope of the pending claims.

We claim:

1. A method for inducing localized hyperthermia in a cell or tissue comprising the steps of delivering nanoparticles to said cell or tissue and exposing said nanoparticles to infrared radiation under conditions wherein said nanoparticles emit heat upon exposure to said infrared radiation.

2. The method of claim 1 wherein the nanoparticles are nanoshells wherein the core material is dielectric or semi-conducting and the shell material is conducting.

3. The method of claim 2 wherein the nanoparticles are nanoshells and have a silica core and the shell is metal.

4. The method of claim 1 wherein the nanoparticles are comprised of silica doped with rare earth emitters.

5. The method of claim 1 wherein the nanoparticles are nanoshells and have a core comprised of gold sulfide and a shell comprised of gold.

6. The method of claim 1 wherein the infrared radiation is of wavelengths from 800 nm to 1300 nm or from 1600 nm to 1850 nm.

7. The method of claim 1 wherein said nanoparticles absorb said radiation.

8. The method of claim 1 further comprising the step of coupling molecules to the nanoparticles wherein said molecules specifically bind to the cell or tissue.

9. The method of claim 8 wherein the binding is by the formation of an antigen-antibody complex.

10. The method of claim 8 wherein the binding is by the formation of a ligand-receptor complex.

11. The method of claim 8 wherein said molecules are coupled to the nanoparticles by a polymer tethering chain.

12. The method of claim 1 wherein said cell is a cancer cell.

13. A method for inducing localized hyperthermia in a cell or tissue comprising the steps of delivering nanoshells to said cell or tissue and exposing said nanoshells to radiation selected from the group consisting of ultrasound, magnetic fields, and electric fields under conditions wherein said nanoshells emit heat upon exposure to said radiation.

14. A method for inducing localized hyperthermia in a cell or tissue comprising the steps of administering nanoshells to an animal and exposing said nanoshells to electromagnetic radiation under conditions wherein said nanoshells emit heat upon exposure to said electromagnetic radiation.

15. The method of claim 14 wherein said animal is human.

16. The method of claim 14 further comprising the step of coupling molecules to the nanoshells wherein said molecules specifically bind to the cell or tissue.

17. The method of claim 16 wherein the binding is by the formation of an antigen-antibody complex.

18. The method of claim 16 wherein the binding is by the formation of a ligand-receptor complex.

19. The method of claim 16 wherein said coupling molecules are antibodies, fragments of antibodies, ligands for specific receptors or proteins binding specifically to the cell or tissue.

20. The method of claim 16 wherein said molecules are coupled to the nanoshells by a polymer tethering chain.

21. The method of claim 20 wherein said polymer tethering chain is a difunctional polyethylene glycol derivative.

22. The method of claim 14 wherein said cells or tissue are cancerous.

23. The method of claim 14 wherein said electromagnetic radiation is selected from the group consisting of ultraviolet, visible, infrared and any combination thereof.

24. The method of claim 23 wherein said electromagnetic radiation is infrared radiation.

25. The method of claim 24 wherein said infrared electromagnetic radiation is between 800 nm and 1300 nm.

26. The method of claim 24 wherein said infrared electromagnetic radiation is between 1600 nm and 1850 nm.

27. The method of claim 24 further comprising the step of coupling molecules to the nanoshells wherein said molecules specifically bind to the cell or tissue.

28. The method of claim 27 wherein the binding is by the formation of an antigen-antibody complex.

29. The method of claim 27 wherein the binding is by the formation of a ligand-receptor complex.

30. The method of claim 27 wherein said coupling molecules are antibodies, fragments of antibodies, ligands for specific receptors or proteins binding specifically to the cell or tissue.

31. The method of claim 27 wherein said molecules are coupled to the nanoshells by a polymer tethering chain.

32. The method of claim 31 wherein said polymer tethering chain is a difunctional polyethylene glycol derivative.

33. The method of claim 14 wherein said nanoshells are encapsulated in a liposome.

34. A method for inducing localized hyperthermia in a cell or tissue comprising the steps of delivering nanoshells to cell or tissue and exposing said nanoshells to radiation selected from the group consisting of ultraviolet, visible, or infrared and any combination thereof under conditions wherein said nanoshells emit heat upon exposure to said radiation.

35. The method of claim 34 further comprising the step of coupling molecules to the nanoshells wherein said molecules specifically bind to the cell or tissue.

36. The method of claim 35 wherein the binding is by the formation of an antigen-antibody complex.

37. The method of claim 35 wherein the binding is by the formation of a ligand-receptor complex.

38. The method of claim 35 wherein said coupling molecules are antibodies, fragments of antibodies, ligands for specific receptors or proteins binding specifically to the cell or tissue.

39. The method of claim 35 wherein said molecules are coupled to the nanoshells by a polymer tethering chain.

40. The method of claim 39 wherein said polymer tethering chain is a difunctional polyethylene glycol derivative.

41. The method of claim 34 wherein said cells or tissue are cancerous.

42. The method of claim 34 wherein said radiation is infrared radiation.

43. The method of claim 42 wherein said infrared radiation is between 800 nm and 1300 nm.

44. The method of claim 42 wherein said infrared radiation is between 1600 nm and 1850 nm.

45. A method for inducing localized hyperthermia in non-cellular non-tissue material comprising the steps of delivering nanoshells to said non-cellular, non-tissue material and exposing said nanoshells to radiation selected from the group consisting of ultraviolet, visible, or infrared and any combination thereof under conditions wherein said nanoshells emit heat upon exposure to said radiation.

46. The method of claim 45 wherein said non-cellular non-tissue material is plaque.

47. A method for denaturing proteins comprising the step of inducing localized hyperthermia comprising the steps of delivering nanoshells to said proteins and exposing said nanoshells to a source of electromagnetic radiation under conditions wherein said nanoshells emit heat upon exposure to said electromagnetic radiation.

48. A method for diagnostic imaging of cell or tissue comprising delivering nanoparticles to the cell or tissue and exposing said nanoparticles to electromagnetic radiation under conditions wherein said nanoparticles illuminate the cell or tissue.

49. The method of claim 48 wherein said electromagnetic radiation is selected from the group consisting of ultraviolet, visible, and infrared radiation.

50. The method of claim 49 wherein said nanoparticles absorb or scatter said radiation.

51. The method of claim 49 wherein said electromagnetic radiation is infrared radiation.

52. The method of claim 48 wherein said nanoparticles act as contrast agents with respect to said radiation.

53. The method of claim 48 wherein the nanoparticles have a core and a shell wherein the core is a dielectric or is semiconducting and the shell is conducting.

54. The method of claim 53 wherein the nanoparticles have a silica core and the conducting shell is metal.

55. The method of claim 53 wherein the nanoparticles have a core comprised of gold sulfide and a shell comprised of gold.

56. The method of claim 48 wherein the nanoparticles are comprised of silica doped with rare earth emitters.

57. The method of claim 56 wherein the rare earth emitter is $Pr^{+3}$, $Er^{+3}$, or $Nd^{+3}$.

58. The method of claim 48 wherein said nanoparticle absorbs, fluoresces, or scatters said radiation.

59. The method of claim 48 further comprising the step of coupling molecules to the nanoparticles wherein said molecules specifically bind to the cell or tissue.

60. The method of claim 59 wherein the binding is by the formation of an antigen-antibody complex.

61. A method for diagnostic imaging of cell or tissue comprising the steps of delivering nanoparticles comprising silica doped with rare earth emitters to the cell or tissue and exposing said nanoparticles to ultraviolet, visible, or infrared radiation, or any combination thereof under conditions wherein said nanoparticles illuminate the cell or tissue.

62. A method for diagnostic imaging of cell or tissue comprising the steps of delivering nanoparticles to the cell or tissue and exposing said nanoparticles to radiation selected from the group consisting of ultrasound, magnetic fields, and electric fields.

63. A method for diagnostic imaging of non-cellular non-tissue material comprising the steps of delivering nanoparticles to the non-cellular non-tissue material and exposing said nanoparticles to radiation selected from the group consisting of ultrasound and electric fields.

64. The method of claim 63 wherein said non-cellular non-tissue material is plaque.

65. A method diagnostic imaging of cell or tissue comprising the steps of administering nanoparticles to an animal and exposing said nanoparticles to electromagnetic radiation wherein said nanoparticles illuminate the cell or tissue of said animal.

66. The method of claim 65 wherein said animal is human.

67. A method diagnostic imaging of non-cellular non-tissue material comprising the steps of administering nanoparticles to an animal and exposing said nanoparticles to electromagnetic radiation wherein said nanoparticles illuminate non-cellular non-tissue material of said animal.

68. The method of claim 67 wherein said animal is human.

* * * * *